United States Patent [19]

Gourlay et al.

[11] Patent Number: 5,415,666
[45] Date of Patent: May 16, 1995

[54] TETHERED CLAMP RETRACTOR

[75] Inventors: Stuart J. Gourlay, Pinole; Terry Buelna, Long Beach; Wayne A. Noda, Mission Viejo; Paul Lubock, Laguna Niguel, all of Calif.

[73] Assignee: Advanced Surgical, Inc., Princeton, N.J.

[21] Appl. No.: 27,505

[22] Filed: Mar. 4, 1993

Related U.S. Application Data

[63] Continuation-in-part of Ser. No. 855,766, Mar. 23, 1992, Pat. No. 5,304,183.

[51] Int. Cl.⁶ .............................................. A61B 17/00
[52] U.S. Cl. ................................. 606/142; 606/148; 606/151; 606/157; 606/139
[58] Field of Search ................ 606/148, 139, 142–144, 606/151, 157, 158, 221; 604/167

[56] References Cited

U.S. PATENT DOCUMENTS

| | | |
|---|---|---|
| 1,274,669 | 8/1918 | Bohn . |
| 2,549,731 | 4/1951 | Wattley . |
| 3,404,677 | 10/1968 | Springer . |
| 3,809,094 | 5/1974 | Cook . |
| 3,877,434 | 4/1975 | Ferguson . |
| 3,994,287 | 11/1976 | Turp et al. ......................... 604/167 |
| 4,046,149 | 9/1977 | Komiya . |
| 4,051,844 | 10/1977 | Chiulli . |
| 4,174,715 | 11/1979 | Hasson . |
| 4,177,813 | 12/1979 | Miller et al. . |
| 4,374,523 | 2/1983 | Yoon . |
| 4,393,872 | 7/1983 | Reznik et al. . |
| 4,519,392 | 5/1985 | Lingua . |
| 4,605,990 | 8/1986 | Wilder et al. . |
| 4,607,620 | 8/1986 | Storz . |
| 4,617,933 | 10/1986 | Hasson ................................ 606/148 |
| 4,681,107 | 7/1987 | Kees, Jr. . |
| 4,706,668 | 11/1987 | Backer . |
| 4,777,949 | 10/1988 | Perlin . |
| 4,779,616 | 10/1988 | Johnson . |
| 4,796,626 | 1/1989 | DeVries . |
| 4,932,955 | 6/1990 | Merz et al. . |
| 4,988,355 | 6/1991 | Leveen et al. . |
| 4,990,157 | 2/1991 | Roberts et al. . |
| 5,022,693 | 6/1991 | Loveless . |
| 5,059,202 | 10/1991 | Liang et al. . |
| 5,074,869 | 12/1991 | Daicoff . |
| 5,074,870 | 12/1991 | von Zeppelin . |
| 5,201,714 | 4/1993 | Gentelia et al. ..................... 604/167 |
| 5,242,456 | 9/1993 | Nash et al. ......................... 606/142 |
| 5,261,895 | 11/1993 | Kablik ................................ 604/167 |

FOREIGN PATENT DOCUMENTS

| | | | |
|---|---|---|---|
| 404226643 | 8/1992 | Japan ................................ 606/222 |
| 1452185 | 10/1976 | United Kingdom . |

OTHER PUBLICATIONS

K. R. Loughlin, "Use of the Scott Ring Surgical Retractor for Illio-inguinal Node Dissection", *British Journal of Urology*, (1988), 60, 367–368.

*Primary Examiner*—Stephen C. Pellegrino
*Assistant Examiner*—Jeffrey A. Schmidt
*Attorney, Agent, or Firm*—Burns, Doane, Swecker & Mathis

[57] ABSTRACT

The invention provides a tissue manipulation system including a tethered clamp, a clamp applicator for positioning the clamp through a trocar sleeve and applying the clamp to a tissue location in the abdominal cavity, and a rigid positioning shaft for engaging the clamp and/or tether to manipulate the clamp. In a further embodiment, the tissue manipulation system includes an introducer through which the tether can be withdrawn from the abdominal cavity and a retainer attached to the proximal end of the introducer for clamping the tether in position. The tissue manipulation system further includes an obturator for inserting the introducer into the abdomen, and a tether snare for retrieving the tether and withdrawing it through the introducer.

79 Claims, 21 Drawing Sheets

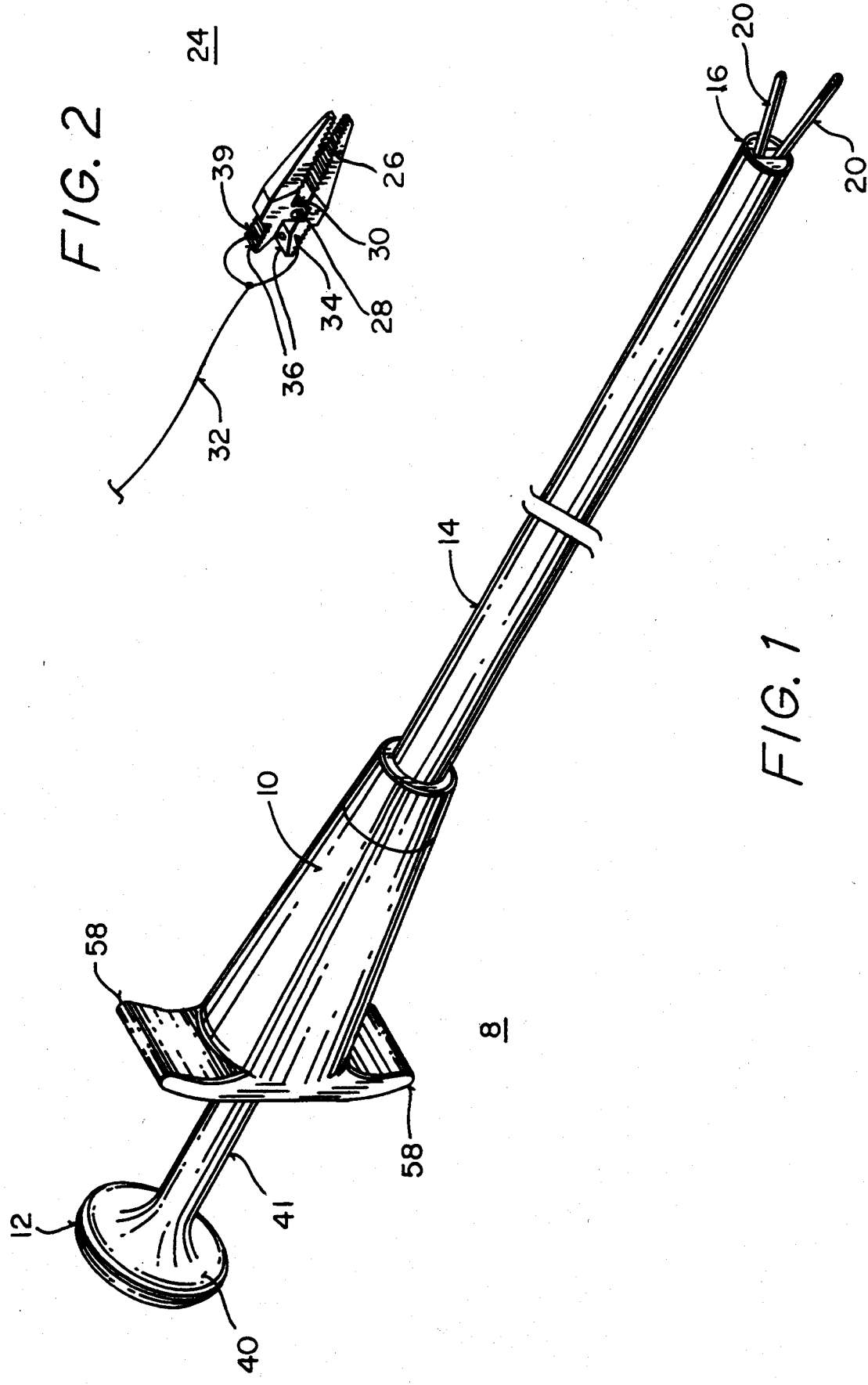

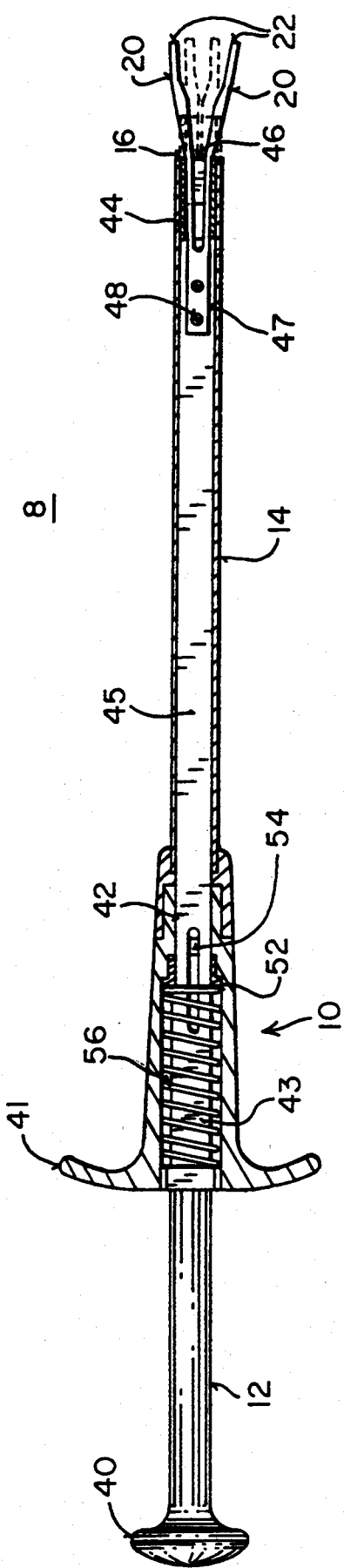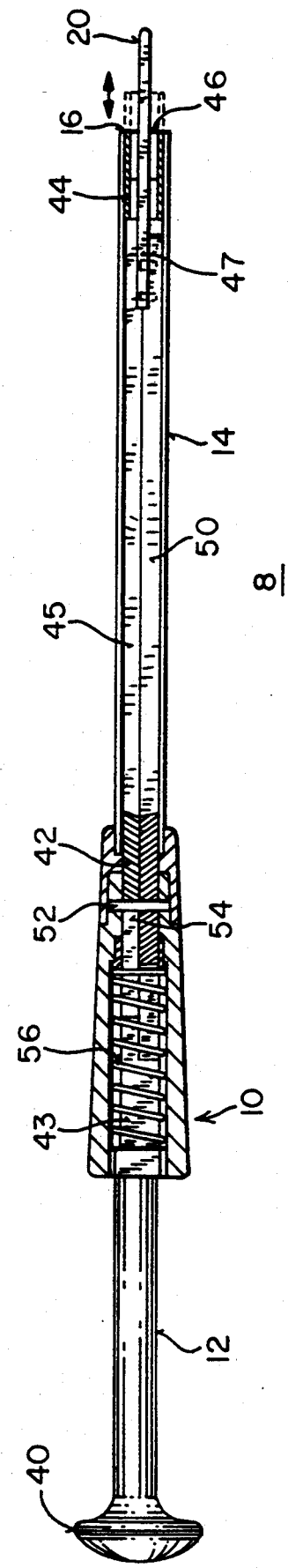
FIG. 3A
FIG. 3B

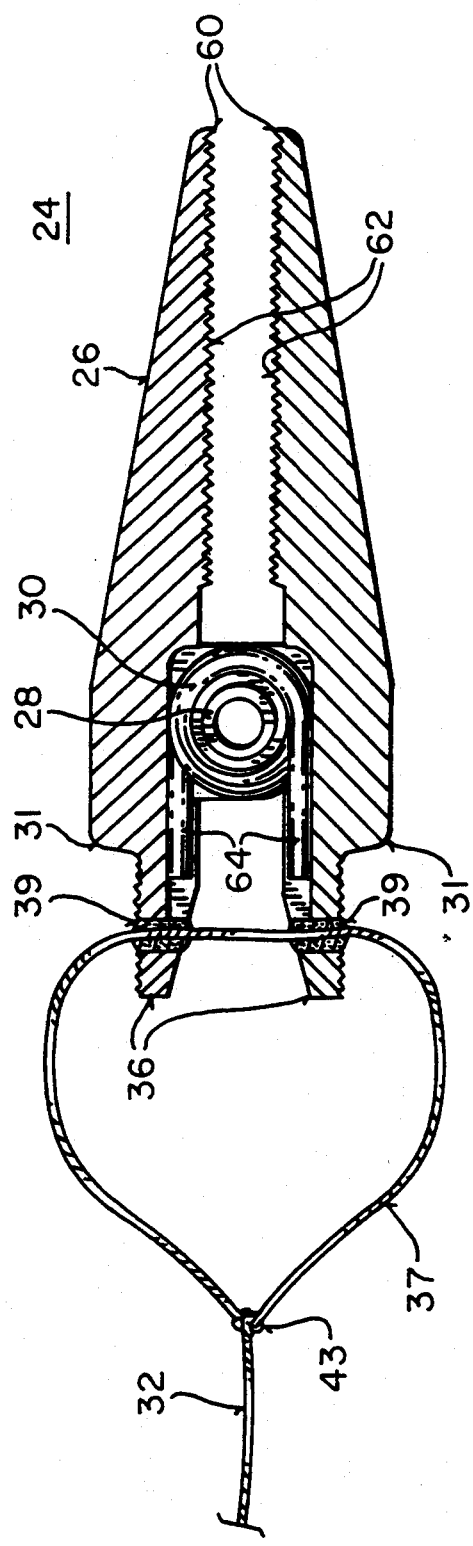
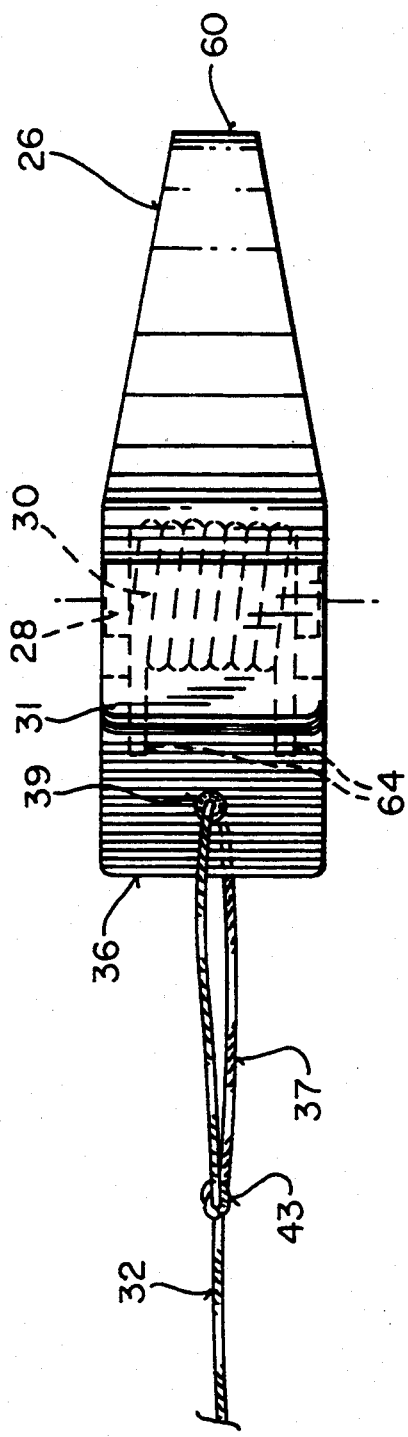

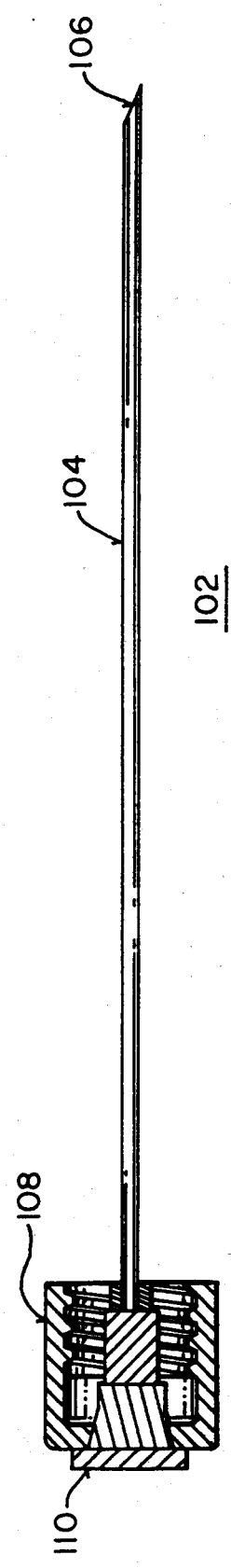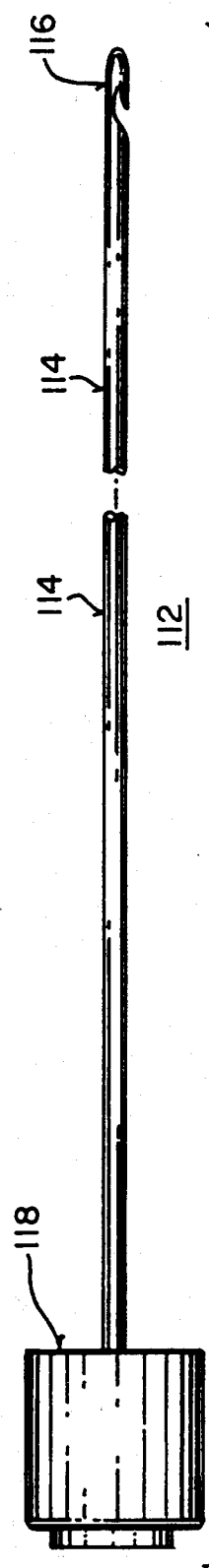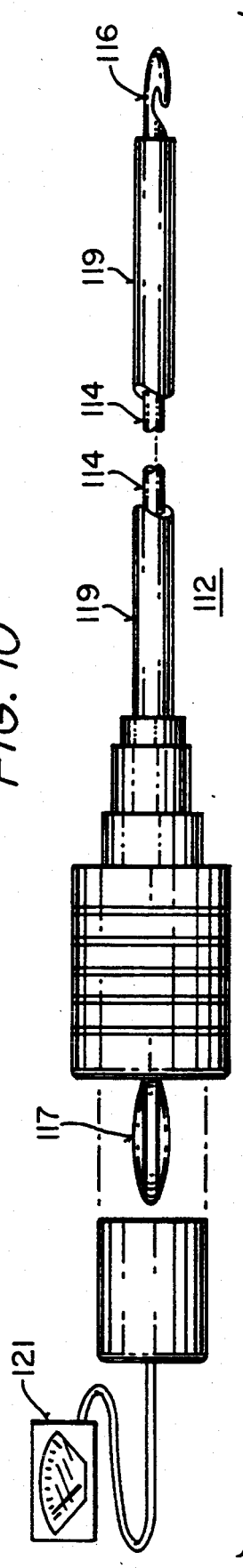
FIG. 9
FIG. 10
FIG. 10A
FIG. 10B

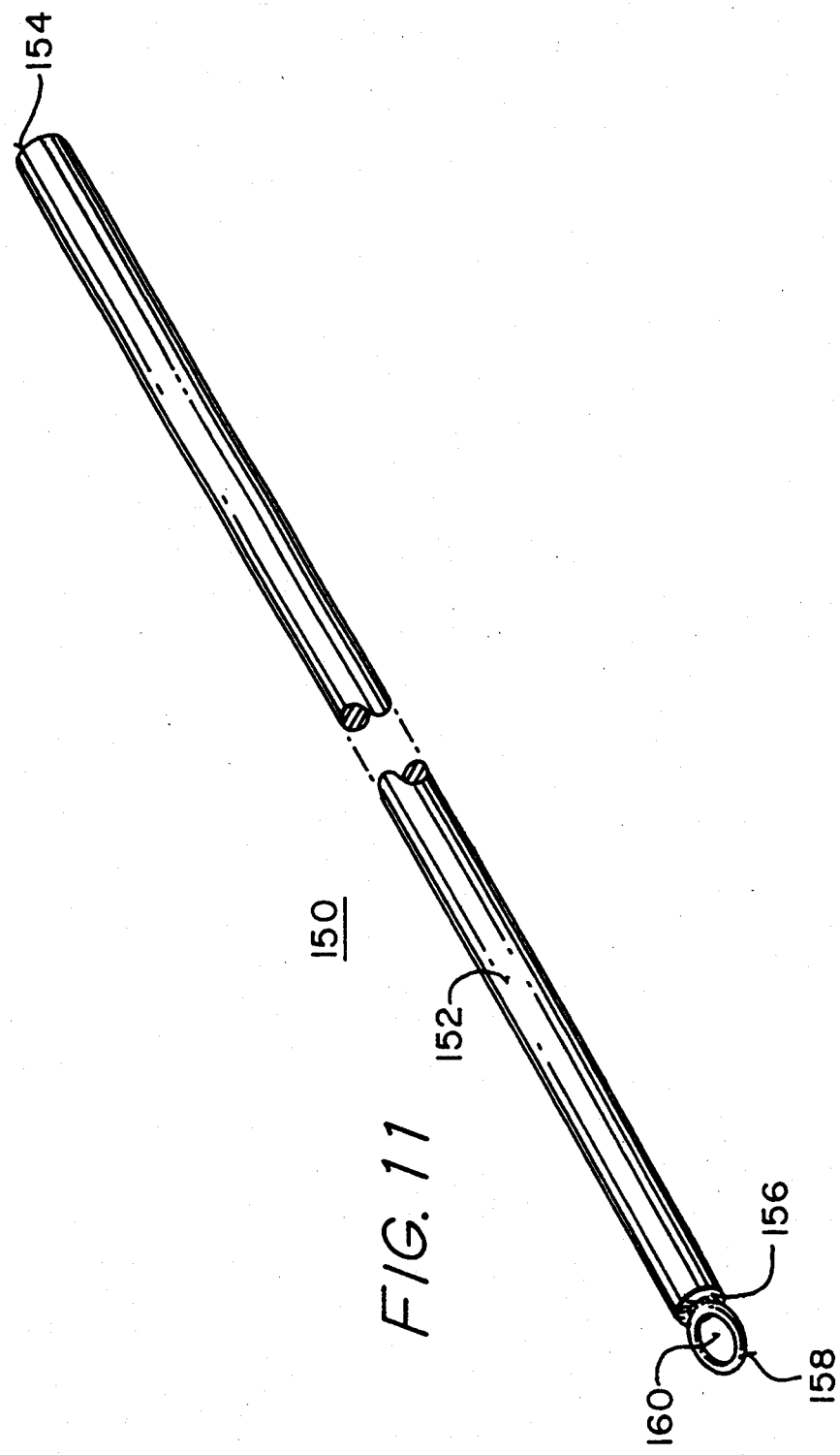

TETHERED CLAMP RETRACTOR

CROSS-REFERENCE TO RELATED APPLICATIONS

This application is a continuation-in-part of application Ser. No. 07/855,766 filed Mar. 23, 1992, entitled "Tethered Clamp Retractor" now U.S. Pat. No. 5,304,183 the complete disclosure of which is incorporated herein by reference.

BACKGROUND OF THE INVENTION

The present invention relates generally to surgical instruments, and more specifically to surgical instruments for tissue manipulation during surgical procedures, especially in laparoscopic surgery of the abdomen.

Laparoscopy facilitates the performance of a variety of surgical procedures of the abdomen, such as cholecystectomies, appendectomies, hernia repairs, hysterectomies and the like, without requiring large incisions or the invasive procedures of conventional surgical techniques. In laparoscopy, the abdominal cavity is distended using gas insufflation, so as to lift the wall of the abdominal cavity away from the underlying organs. A video scope is inserted through a cannula or trocar sleeve into the abdomen and connected to a monitor so as to provide visual guidance to the surgeon. One or more additional trocar sleeves are placed in the abdomen to allow introduction of surgical tools, such as retractors, cutting instruments and the like. Such trocar sleeves have a sealed passage through which instruments may be inserted, providing a leak-resistant entryway into the insufflated abdomen.

One disadvantage of laparoscopic surgical procedures is the limited access to the surgical site available to the surgeon. Entry to the site is limited to the small incisions or trocar sleeves through the abdominal wall. Any manipulation of internal tissue, for example, positioning a duct for ligation, or moving tissue to allow better access to or visibility of a particular location, must be performed using long handled instruments insertable through the trocar sleeves or incisions.

It is known to use surgical clips or clamps for the purpose of clamping vessels or manipulating tissue. Typically, such clamps have a pair of movable jaws biased by a spring into a closed position, allowing the clamp to be placed on a vessel or portion of tissue and be firmly retained thereon. Examples of such clamps can be seen in U.S. Pat. No. 4,932,955 to Merz et al., U.S. Pat. No. 4,605,990 to Wilder et al., U.S. Pat. No. 5,074,870 to Von Zeppelin, U.S. Pat. No. 3,809,094 to Cook, U.S. Pat. No. 3,404,677 to Springer and U.S. Pat. No. 4,051,844 to Chiulli and U.S. Pat. No. 4,988,355 to Leveen et al.

It is also known in laparoscopic surgical procedures to use long-handled instruments for applying clamps to internal tissue within the abdominal cavity. Such clamp applicators typically include a pair of movable handles at the proximal end of the applicator and a pair of movable jaws at the distal end, wherein a clamp is placed in the jaws, the distal end of the applicator is inserted through a trocar sleeve into the abdomen and positioned at the desired tissue location, and the handles are actuated so as to apply the clamp to the tissue. Illustrative examples are seen in U.S. Pat. No. 4,174,715 to Hasson, and British Patent No. 1,452,185 to Wolf. Other tissue manipulation or clamping instruments with possible application to laparoscopic procedures are seen in U.S. Pat. No. 4,607,620 to Storz, U.S. Pat. No. 5,074,869 to Daicoff, U.S. Pat. No. 4,393,872 to Reznik et al., U.S. Pat. No. 2,549,731 to Wattley and U.S. Pat. No. 1,274,669 to Bohn.

However, known devices for manipulating tissue in laparoscopic procedures suffer from certain disadvantages. Known manipulating instruments typically have long, rigid members between the distal end and the handles at the proximal end, limiting the positionability of such devices. In addition, once such devices have been used to manipulate tissue to a desired position, the devices must be held in that position by the surgeon or an assistant. Further, the usefulness of known devices for positioning of tissue during laparoscopic procedures is limited by the necessity of having a trocar sleeve or incision in place proximate to the tissue to be manipulated in addition to those trocar sleeves being used for the surgical instruments employed in the procedure. Moreover, the size of known manipulation instruments requires that the additional trocar sleeve be of considerable size (e.g. 10 mm), increasing the invasiveness of the procedure.

In certain procedures, it is further desirable to be able to manipulate tissue in various directions, including both toward and away from the point of access (e.g. incision or percutaneous cannula) into the body. This is particularly true, for example, for the retraction of the gallbladder during laparoscopic cholecystectomy procedures. In such procedures, using a system which allows retraction of the gallbladder toward the surgeon, a cannula is optimally placed high into the rib cage through which the retraction device is introduced. However, this poses a significant risk of patient injury due to the close proximity to the diaphragm. To eliminate this risk, the cannula is ideally placed in a lower position below the ribs. However, this requires a retraction system which facilitates retraction in a direction away from the position of the cannula (and the surgeon).

For these and other reasons, an improved system and method for manipulating internal tissue during laparoscopic and other surgical procedures is desired. The system and method should allow greater flexibility in positioning from various points and at various angles, including both toward and away from the surgeon. The system and method should allow positioning through a trocar sleeve or similar small access way and should minimize the need for placement of trocar sleeves in addition to those already in place for insertion of surgical instruments. Further, the system and method should allow the tissue to be maintained in a desired position without the need for ongoing manual intervention by the surgeon or an assistant.

SUMMARY OF THE INVENTION

The present invention provides a system and method for manipulating tissue and body structures in various surgical procedures, having particular usefulness in minimally-invasive procedures such as laparoscopic and endoscopic surgery. The invention allows internal tissue to be manipulated through a trocar sleeve or similar accessway and is highly flexible for positioning tissue from various angles. The system and method are simple and convenient, and do not require ongoing manual intervention once the tissue has been manipulated into a desired position. While being especially well-suited to minimally-invasive surgical techniques such as laparoscopy, endoscopy, thoracoscopy and arthroscopy, the tissue manipulation system and method of the invention are useful in any of a multitude of surgical procedures, including conventional open surgical procedures.

In one aspect of the invention, a tissue manipulation system comprises a clamp having a pair of movable jaws and means for closing and opening the jaws; means for applying the clamp to a first tissue site; and a flexible tether having a first end attached to the clamp and a free end opposite the first end for remotely manipulating the clamp in a first direction. The system may further include a rigid positioning shaft having a distal end for engaging one of either the clamp or the tether, and a proximal end for pushing on the shaft to manipulate the clamp in a second direction. In an exemplary embodiment, the positioning shaft will be configured to engage a knot in the tether near the first end where it attaches to the clamp.

Usually, the means for applying the clamp comprises a clamp applicator having an elongated body with a distal end, a proximal end and an axial passageway therebetween; a pair of movable arms disposed at the distal end and configured to engage the means for closing and opening the jaws of the clamp; means at the proximal end of the body for actuating the arms; and a linkage disposed in the axial passageway, the linkage coupling the arms to the means for actuating. The clamp is preferably engaged by the clamp applicator such that the clamp may be rotationally positioned about at least 180° relative to the applicator.

In a further embodiment, the tissue manipulation system further includes means for retrieving the free end of the tether. Usually, the means for retrieving the tether comprises an elongated snare having a hooked end for grasping the tether.

Preferably, the tissue manipulation system further comprises means separated from the clamp for retaining the tether, so as to maintain the tissue in a desired position. In a preferred embodiment, the means for retaining the tether comprises an elongated cylindrical introducer having a distal end, a proximal end and an axial passageway therebetween, and a retainer disposed at the proximal end of the introducer, whereby the tether may be drawn through the axial passageway and detachably secured in the retainer. Usually, the means for retrieving the tether is inserted through the introducer so as to draw the tether back through the introducer and into the retainer. By tensioning the tether, the tissue can be manipulated into position, and maintained in position by locking the tether in the retainer. In a preferred embodiment, the retainer comprises a stopcock attached to the proximal end of the introducer.

In a preferred embodiment, the positioning shaft will be insertable through the axial passage of the introducer. The positioning shaft will usually include means for guiding the distal end toward the clamp, which preferably will comprise a loop at the distal end of the shaft having an eye through which the free end of the tether may pass. In this way the free end of the tether may be brought out of the body cavity through the introducer and threaded through the eye in the loop, the shaft then being inserted through the introducer and guided along the tether toward the clamp. The knot near the first end of the tether will engage the eye in the loop and prevent further movement along the tether, providing a point from which the clamp can be manipulated in a direction away from the introducer.

In a further aspect of the invention, a method for manipulating tissue comprises the steps of introducing a clamp through a percutaneous introducer to a tissue location; securing the clamp to the tissue location; and engaging a flexible tether attached to the clamp with a distal end of a rigid positioning shaft to manipulate the tissue in a first direction. The method may further include tensioning a free end of the tether to manipulate the tissue in a second direction. In this way the system facilitates manipulation of tissue either toward or away from the surgeon by tensioning the tether or pushing on the positioning shaft. Conveniently, the clamp may be introduced using a clamp applicator inserted through a trocar sleeve or cannula or equivalent.

Preferably, the step of tensioning the free end of the tether comprises pulling the free end through a percutaneous introducer. In addition, the method optionally includes the step of securing the tether relative to the introducer after tensioning the tether, usually by actuating a retainer disposed at the proximal end of the introducer. The positioning shaft may be inserted through the introducer and guided toward the clamp by threading the free end of the tether through the loop at the distal end of the shaft. The method may also include the step of retrieving the free end of the tether to facilitate removing the clamp from the tissue location.

In a further embodiment, the tether may be internally secured to a second clamp, hook or other tissue engaging means attached to a second internal tissue location. In still another embodiment, the tether is secured to a structure outside of the body cavity, such as the surgical drapes.

The introducer is percutaneously positioned, in one embodiment, by placing an obturator in the introducer and piercing through tissue at the desired location. In another embodiment, the introducer is positioned by applying energy such as radiofrequency current to the tissue by means of an electrode situated at the distal end of the introducer.

The tether retrieving means may also be positioned without the use of an introducer. In this embodiment, the tether retrieving means will have means for penetrating tissue at its distal end, such as a sharpened tip or an RF electrode, whereby the retrieving means is directly introduced into the body cavity by penetrating tissue with the distal end. The tether may then be retrieved and secured to a second tissue structure within the body cavity, or more usually drawn out of the body cavity and externally secured, typically to the patient's skin using a clamp, tape, or any other temporary fastening means.

In a particular embodiment, the method is used for retraction of the gallbladder during, for example, a laparoscopic cholecystectomy. In such a case, the introducer may be positioned below the ribs, allowing retraction of the gallbladder away from the introducer by pushing on the tether and/or clamp using the positioning shaft. This eliminates the risk of injury inherent in placement of the cannula higher in the rib cage near the diaphragm. During the procedure, the method may further include distending the abdominal cavity using insufflation, and the use of a laparoscope for visualization.

It should be understood that while the invention is described in the context of laparoscopic surgery of the abdomen, the tissue manipulation system and method disclosed herein are equally useful in other types of surgery, e.g. surgery of the pelvis or thorax, as well as in open surgical procedures.

A further understanding of nature and advantages of the invention may be realized by reference to the remaining portions of the specification and the drawings.

BRIEF DESCRIPTION OF THE DRAWING

FIG. 1 is a perspective schematic of a clamp applicator constructed in accordance with the principles of the present invention.

FIG. 2 is a perspective view of a tethered clamp constructed in accordance with the principles of the present invention.

FIGS. 3A-3B are a front and top cross-sectional views, respectively, of the clamp applicator of FIG. 1.

FIGS. 4A and 4B are front and top elevational views of the tethered clamp applicator of the present invention.

FIG. 9 is a front elevational view of an obturator for introducing the introducer/stopcock assembly of FIG. 7.

FIG. 10 is a front elevational view of a tether snare constructed in accordance with the principles of the present invention.

FIGS. 10A-10B are front elevational views of alternative embodiments of the tether snare of FIG. 9.

FIG. 11 is a perspective view of the positioning shaft of the invention.

DETAILED DESCRIPTION OF THE ILLUSTRATIVE EMBODIMENTS

Figure 5B:
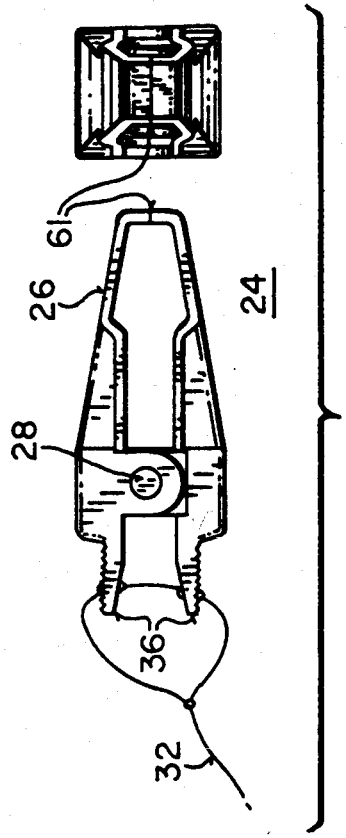
FIGS. 5A-5D are front and end elevational views of various embodiments of the tethered clamp of FIG. 2.
Figure 5D:
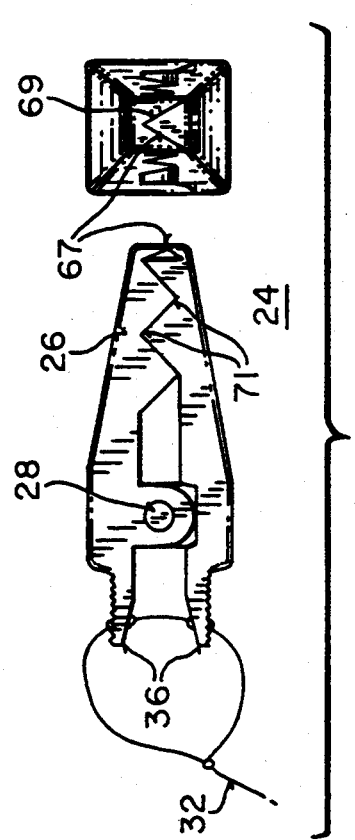

In a preferred aspect Of the present invention, a tissue manipulation system includes a clamp, a flexible tether attached to the clamp, and a clamp applicator for positioning the clamp through a trocar sleeve or other cannula and applying the clamp to a tissue location. The system may further include a rigid positioning shaft configured to engage the clamp and/or the tether to facilitate manipulation of tissue. In a further embodiment, the tissue manipulation system comprises an introducer and a retainer attached to the proximal end of the introducer for retaining the tether. The system may further include an obturator or an RF electrode for percutaneously inserting the introducer. The invention also provides a tether snare for retrieving the tether, which may be inserted through the introducer to draw the tether through the introducer to the retainer. Alternatively, the tether snare may be provided with means for penetrating tissue to directly introduce the tether snare without need for the introducer or other cannula.

Referring to FIG. 1, the clamp applicator comprises a tubular handle 10, typically composed of polycarbonate or polysulfone, with a plunger 12 slidably mounted in handle 10. Tubular extension 14, usually of polycarbonate or stainless steel, extends from the handle 10 distally and has an aperture 16 at its distal end.

Plunger 12 is coupled to a pair of movable arms 20 having a proximal portion disposed within extension 14 and a distal portion extending from the distal end of extension 14. Arms 20 have a pair of tips 22 for engaging the tethered clamp, which preferably have serrations on the inner surfaces thereof.

As seen in FIG. 2, tethered clamp 24 has a pair of movable jaws 26 connected at hinge 28 and biased in a closed configuration by spring 30. A lever 36 is attached to each of jaws 26 for opening and closing thereof. Levers 36 will have a flat lateral surface for engagement by arms 20 of applicator 8. Flexible tether 32 is attached to a proximal portion 34 of levers 36 through a hole 39, which is usually filled with adhesive.

Referring to FIGS. 3A and 3B, clamp applicator 8 will be described in greater detail. Handle 10 includes a pair of grips 41 configured to be grasped by the user's fingers when plunger 12 is depressed with the thumb. Usually, plunger 12 will have a knob, ring or other means 40 to facilitate application of pressure in the distal direction. Plunger 12 is connected to a shaft 42 extending through handle 10. A proximal portion 43 of shaft 42 is preferably circular in cross-section, while a distal portion 45 has a semicircular cross-section and extends distally through extension 14. The distal end of shaft 42 is connected to a tubular sleeve 44 slidably disposed within extension 14 near its distal end. Sleeve 44 has a rectangular aperture 46 at its distal end through which arms 20 extend, whereby distal movement of sleeve 44 causes arms 20 to close toward one another. Shank 47 of arms 20 is fixed via pins 48 to arm support member 50 (FIG. 3B), which is fixed at its proximal end to handle 10 by a pin 52. Pin 52 extends through a longitudinal slot 54 in shaft 42 to allow axial movement thereof. A spring 56 is disposed about shaft 42 and is engaged by a retainer 58 fixed to shaft 42 to bias plunger 12 in a proximal position, such that arms 20 are in an open configuration when pressure is released.

Figure 5A:
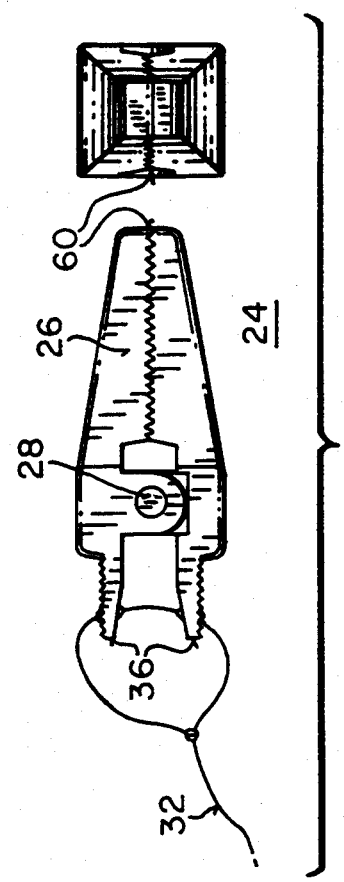
Figure 5C:
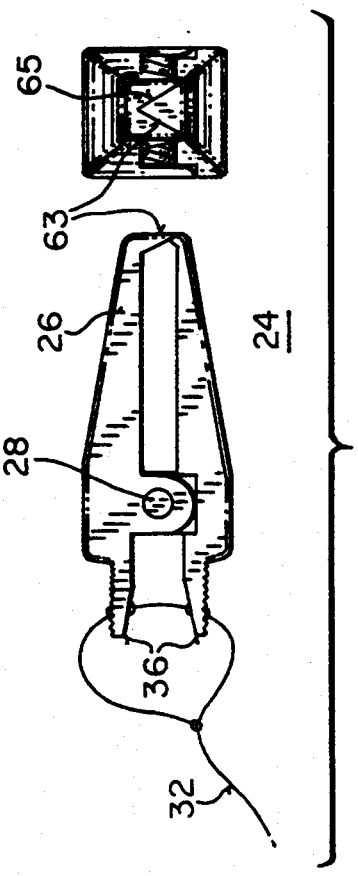

Referring now to FIGS. 4A-4B and 5A-5D, the tethered clamp 24 of the present invention will be described. Clamp 24 has a pair of movable jaws 26 having a contact plane 60 for engaging tissue when jaws 26 are closed. In an "Atraumatic" embodiment, contact plane 60 has a plurality of teeth 62 for improved grip on tissue, as shown in FIG. 5A. FIG. 5B illustrates a "Babcock" configuration, with jaws 26 meeting along a narrow, straight surface 61 at the distal end of the jaws. FIG. 5C illustrates the "Kocher" type, with jaws 26 meeting at an overlapping point 63 and notch 65 at the distal end of the jaws. In the "traumatic" type of FIG. 5D, jaws 26 meet in a point 67 and notch 69 at the distal end as in the "Kocher" type, and further contact each other along teeth 71 proximal to the distal end. Other well-known clamp designs include, for example, Kelly, Allis, Glassman, Bulldog, DeBakey, and Cooley-type clamps, any of which may be used in conjunction with the present invention.

Jaws 26 are joined at hinge 28, which may comprise a pin or rivet. Spring 30 is disposed around hinge 28, with a pair of extensions 64 engaging levers 36. Spring 30 is configured to bias jaws 26 in a closed configuration by exerting outward force against levers 36. Tether 32 extends through holes 39 in levers 36 and is tied to itself by a knot 43 forming a knotted loop 37. Preferably, holes 39 are filled with an adhesive. Tether 32 preferably comprises medical grade monofilament polyester, polyamide or polypropylene line load rated to 10 lbs. Alternatively, tether 32 may be elastic, so as to be resiliently extendable. Levers 36 are engaged by tips 22 so as to permit clamp 24 to be rotationally positioned relative to clamp applicator 8 about an axis through tips 22. Preferably, levers 36 have a serrated surface for improved grip on the clamp by arms 20 of clamp applicator 8.

In an alternative embodiment, a second clamp, hook, or other tissue engaging means may be detachably coupled to the free end of the tether or to a point along the tether between the clamp and the free end. In this embodiment, the tether is tensioned to position the clamp 24, and the tissue engaging means coupled to the tether is attached to a second portion of tissue to maintain clamp 24 in position (see FIG. 22, described below).

Figure 6A:
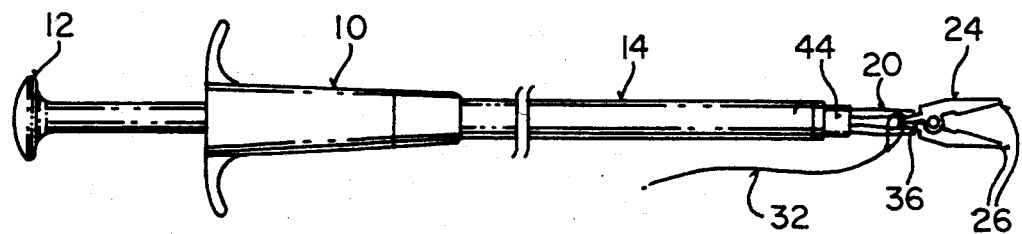
FIGS. 6A-6D are front elevational views illustrating the operation of the clamp applicator and tethered clamp of FIGS. 1 and 2.
Figure 6B:
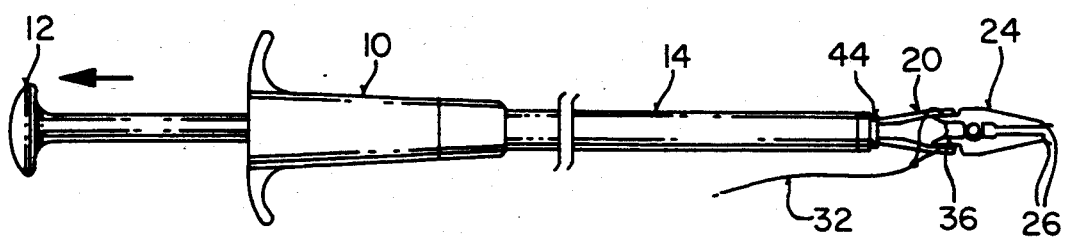
Figure 6C:
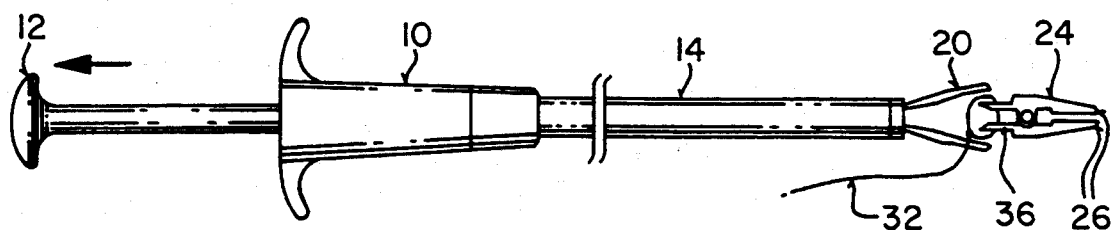
Figure 6D:
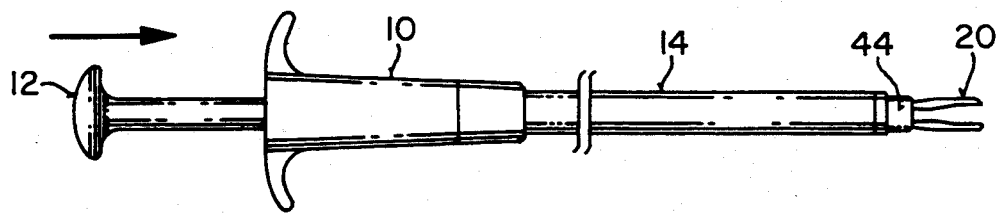

The operation of clamp applicator 8 is illustrated in FIGS. 6A–6D. Tethered clamp 24 is positioned between arms 20 and plunger 12 is depressed to firmly engage the arms against levers 36 of the clamp. By further depressing plunger 12, tubular sleeve 44 is extended so as to press levers 36 together, thereby opening jaws 26. Allowing plunger 12 to retract causes levers 36 to move apart, closing jaws 26. As shown in FIG. 6C, when plunger 12 is in its fully retracted position, the gap between arms 20 is wider than the distance between levers 36, allowing the clamp applicator to be disengaged from clamp 24.

Conveniently, the tethered clamp of the invention may also be introduced into a body cavity and applied to a tissue structure by means of a conventional needle holder in lieu of clamp applicator 8. Needle holders and other types of grasping forceps are well-known for grasping a suture needle or tissue structure for purpose of suturing, ligating or manipulating a tissue structure. In the present invention, a needle holder may be used for grasping levers 36 of the tethered clamp and introducing the clamp by inserting the needle holder through a trocar sleeve. In a specific embodiment, a reducer sleeve of well-known construction will further be provided to facilitate introduction of a needle holder of reduced diameter, e.g. about 5 mm, through a trocar sleeve of, for example, 10–12 mm diameter. Needle holders as well as reducer sleeves suitable for use in the system of the present invention are described in U.S. Pat. No. 5,211,650, application Ser. No. 07/912,353, the complete disclosure of which is incorporated herein by reference.

Figure 7:
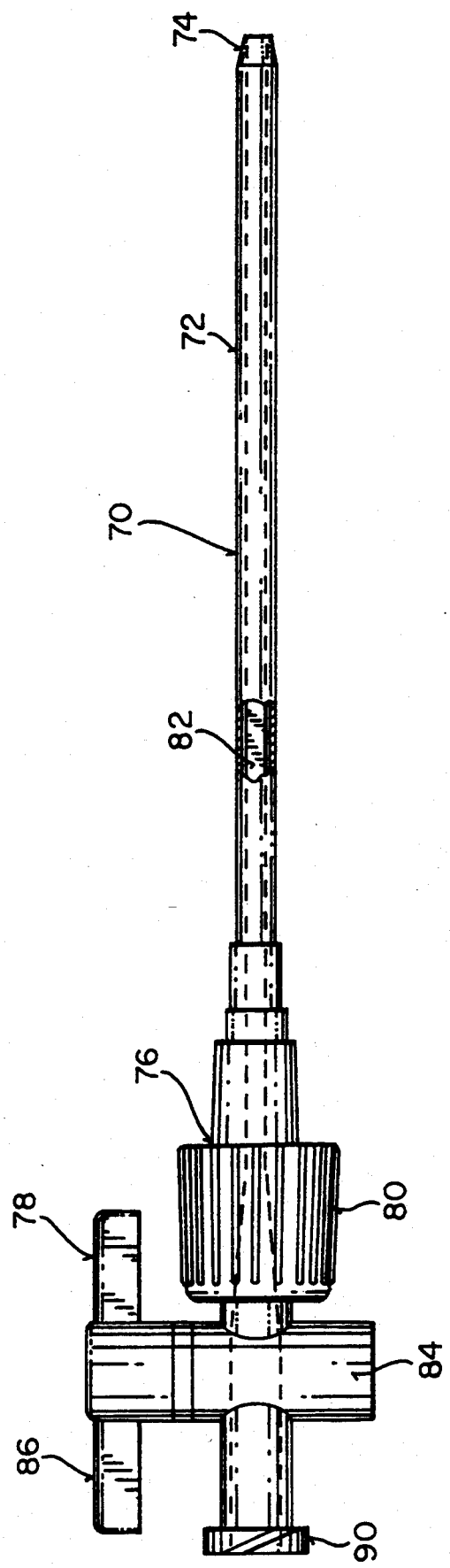
FIG. 7 is a front elevational view of an introducer and stopcock assembly constructed in accordance with the principles of the present invention.
Figure 7A:
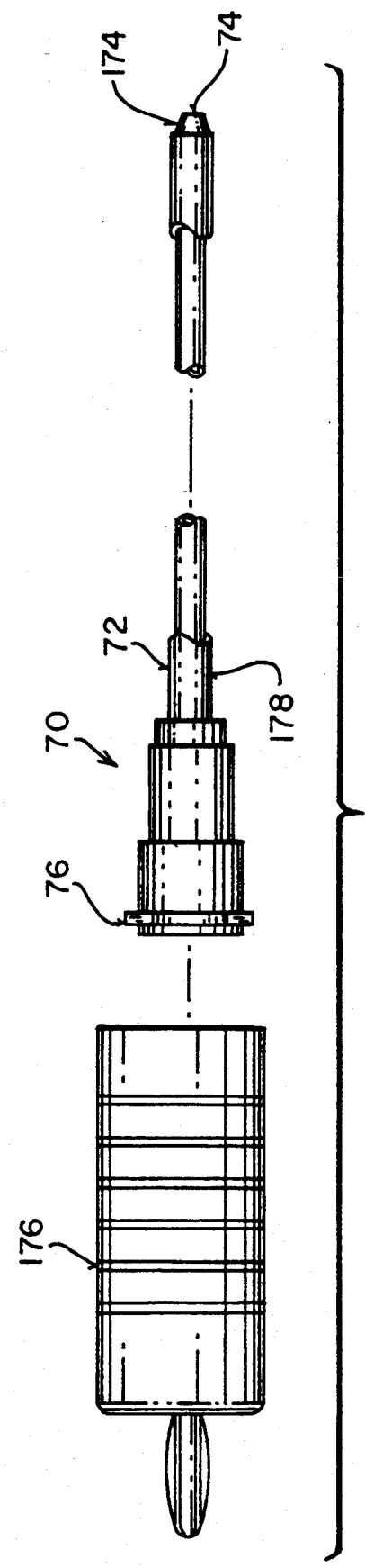
FIG. 7A is a front elevational view of an alternative embodiment of the introducer of FIG. 7.

Referring now to FIGS. 7–7A, the introducer/stopcock assembly will now be described. Introducer 70 comprises a tubular shaft 72, usually of medical grade polyurethane, PVC or polyethylene, having a taper 74 at its distal end and a female luer lock 76 or other mounting means at its proximal end. Stopcock 78 has a male luer lock 80 which attaches to female luer lock 76 of introducer 70, forming a gas-tight seal to prevent gas from the insufflated abdominal cavity from escaping. An axial passageway 82 extends from the distal end of introducer 70 to its proximal end at luer lock 76. Stopcock 78 includes a valve assembly 84 having a valve handle 86 for opening and closing valve 84.

Figure 8A:
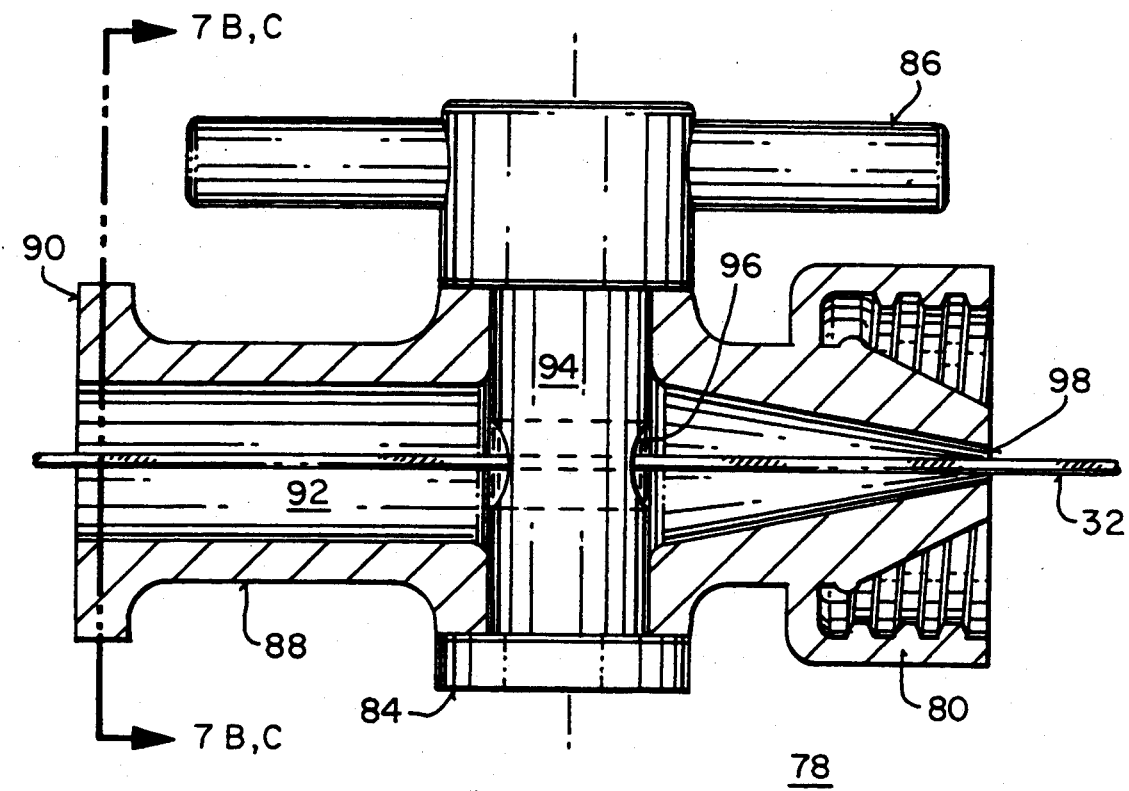
FIG. 8A is a front cross-sectional view of the stopcock of the FIG. 7.
Figure 8B:
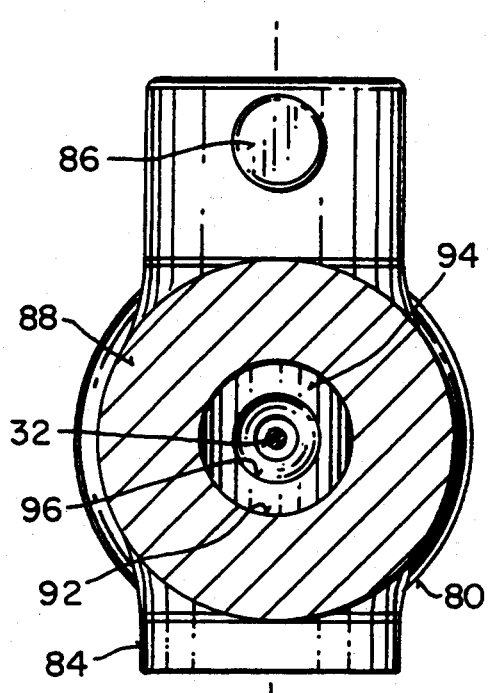
FIGS. 8B and 8C are top cross-sectional views of the stopcock of FIG. 7.
Figure 8C:
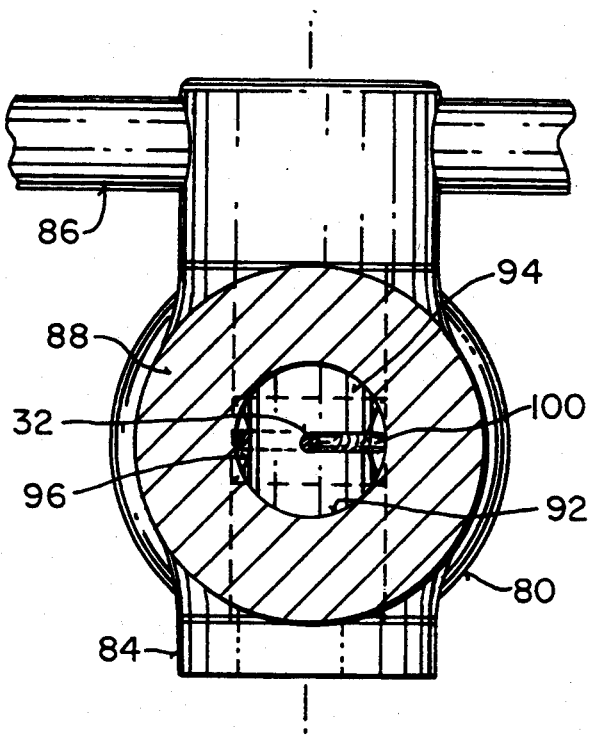

Referring to FIGS. 8A–8C, stopcock 78 includes a body 88 with a male luer lock 80 at its distal end and female luer lock 90 at its proximal end, with an axial passageway 92 extending therebetween. Valve 84 extends transversely through a middle portion of body 88, and includes a rotatable shaft 94 attached to valve handle 86. Shaft 94 has an orifice 96 which, when valve 84 is in an open position, is aligned with axial passageway 92. When valve 84 is closed by rotating handle 86 90°, providing an air tight seal between distal end 98 and shaft 94.

The introducer/stopcock assembly also serves to retain tether 32 in tension so as to maintain tethered clamp 24 in a desired position. As shown in FIG. 8A, tether 32 can be drawn through introducer 70 and through axial passageway 92 and orifice 96 of stopcock 78. By tensioning tether 32, tethered clamp 24 and the tissue to which it is clamped may be positioned, and this position maintained by rotating valve handle 86 on stopcock 78. When valve 84 is in an open position, as shown in FIG. 8B, tether 32 extends relatively straight through orifice 96 and axial passageway 92. When handle 86 is rotated 90°, as in FIG. 8C, orifice 96 is rotated so as to extend transversely to axial passageway 92, jamming portions of tether 32 against walls 100 of axial passageway 92 so as to clamp tether 32 firmly in position.

In a further embodiment of the invention, an obturator 102 is provided for percutaneously inserting introducer 70 into the abdomen or other body cavity. As shown in FIG. 9, obturator 102 includes a needle 104, usually comprising a 14 gauge needle of surgical steel. Needle 104 has a sharp point 106 for piercing the skin or other tissue. At the proximal end of needle 104 is a hub 110 which will usually be elongated for grasping by the user. An interconnect 108, typically comprising a male luer lock, may also be provided for connection to stopcock 78. Needle 104 may be inserted through stopcock 78 and introducer 70, with point 106 extending from the distal end 74 of the introducer. Male luer lock 108 engages female luer lock 90 at the proximal end of stopcock body 88 to prevent gas leakage through stopcock 78 when obturator 104 is positioned through the introducer.

As an alternative to obturator 102 for introduction, introducer 70 may be provided with an electrode at its distal end 74 through which energy may be applied to tissue for penetration thereof. As illustrated in FIG. 7A, the electrode 174 will be coupled to an electrical connector 176 at the proximal end of introducer 70 which may be connected to an energy source, such as a thermal, ultrasonic or RF generator. In an exemplary embodiment, electrode 174 will comprise the distal end 74 of shaft 72, which is composed of a conductive metal such as stainless steel. Shaft 72 is preferably covered by an insulative sleeve 178, which leaves only distal tip 74 exposed. Connector 176 is electrically coupled to proximal end 76 of shaft 72, such that energy (e.g. RF current) is conducted from connector 176 through shaft 72 to distal tip electrode 174.

The invention further provides means for retrieving the tether 32 of tethered clamp 24. As shown in FIG. 10, in a preferred embodiment, the means for retrieving the tether comprises a tether snare 112 having an elongated rod 114, usually of stainless steel, with a hook 116 at its distal end. A male luer lock 118 and, desirably, a handle to facilitate manipulation, are attached to the proximal end of rod 114. When the introducer/stopcock assembly is in position in the abdomen, rod 114 of tether snare 112 may be inserted through stopcock 78 and introducer 70 such that hook 116 extends from the distal end of introducer 70. To prevent leakage of gas from the abdomen, male luer lock 118 engages with female luer lock 90 at the proximal end of stopcock 78. Tether snare 112 may then be positioned to retrieve tether 32 in hook 116 by tilting and/or rotating the introducer/stopcock assembly or longitudinally repositioning tether snare 112 within introducer 70. When tether 32 has been engaged by hook 116, male luer lock 118 may be released from luer lock 90 and tether snare 112 withdrawn from the introducer/stopcock assembly, drawing tether 32 through axial passageway 82 of introducer 70, and axial passageway 92 of stopcock 78.

In an alternative embodiment, illustrated in FIG. 10A, the tether snare is provided with an electrical connector 117 for connection to an electro-surgical generator 121. Generator 121 may supply thermal, ultrasonic or radiofrequency energy to the tether snare through connector 117. Connector 117 is coupled to rod 114. When current is supplied from the generator through the connector 117, hooked end 116 may be used to apply energy to the tissue at the desired site for introducing the tether snare. In an exemplary embodiment, connector 117 is connected to a radiofrequency (RF) electrosurgical generator 121, and the tether snare is percutaneously inserted by applying RF energy to the tissue. Hooked end 116 will preferably have a tapered distal tip to facilitate penetration through tissue using ultrasonic, thermal or RF ablation. Usually, an insulative sleeve 119 will be provided about rod 114 proximally of hooked end 116 so that current is conducted only through the hooked end. Tether snare 112 is thereby introduced without the need to position introducer 70 or other cannula as an access port to the body cavity.

In a further embodiment, illustrated in FIG. 10B, hooked end 116 is formed in a sharp point, facilitating penetration of tissue by application of a distally-directed force to tether snare 112. As in the embodiment of FIG. 10A, the pointed hooked end 116 of tether snare 112 allows the snare to be introduced without the need for introducer 70 or other cannula. In an alternative embodiment, the sharpened point of hooked end 116 will be retractable, as in a Veress-type needle.

The positioning shaft of the invention is illustrated in FIG. 11. Positioning shaft 150 comprises a rigid rod 152 having a proximal end 154 and a distal end 156. Rod 152 will typically be of surgical steel, and will have a diameter of minimal size, but one large enough to have sufficient column strength to allow a distal force to be applied to the rod without significant bending or deformation. In an exemplary embodiment, the rod is 13 gauge. The distal end 156 is configured to engage clamp 24 and/or tether 32, and will usually include a wire loop 158 having an eye 160 large enough for tether 32 to pass through. This permits the free end of the tether to be threaded through eye 160 so that the shaft may be guided toward the clamp along the tether. Loop 158 may be formed by bending the distal end of rod 152 to form eye 160, or may be a separate piece of wire, usually of surgical steel, fixed to distal end 156 by adhesive, welding or the like. The shaft may be guided along tether 32 toward the clamp until knot 43 engages eye 160, at which point further distal movement of shaft 150 will push clamp 24 away from the user to re-position the tissue to which the clamp is attached.

Figure 12:
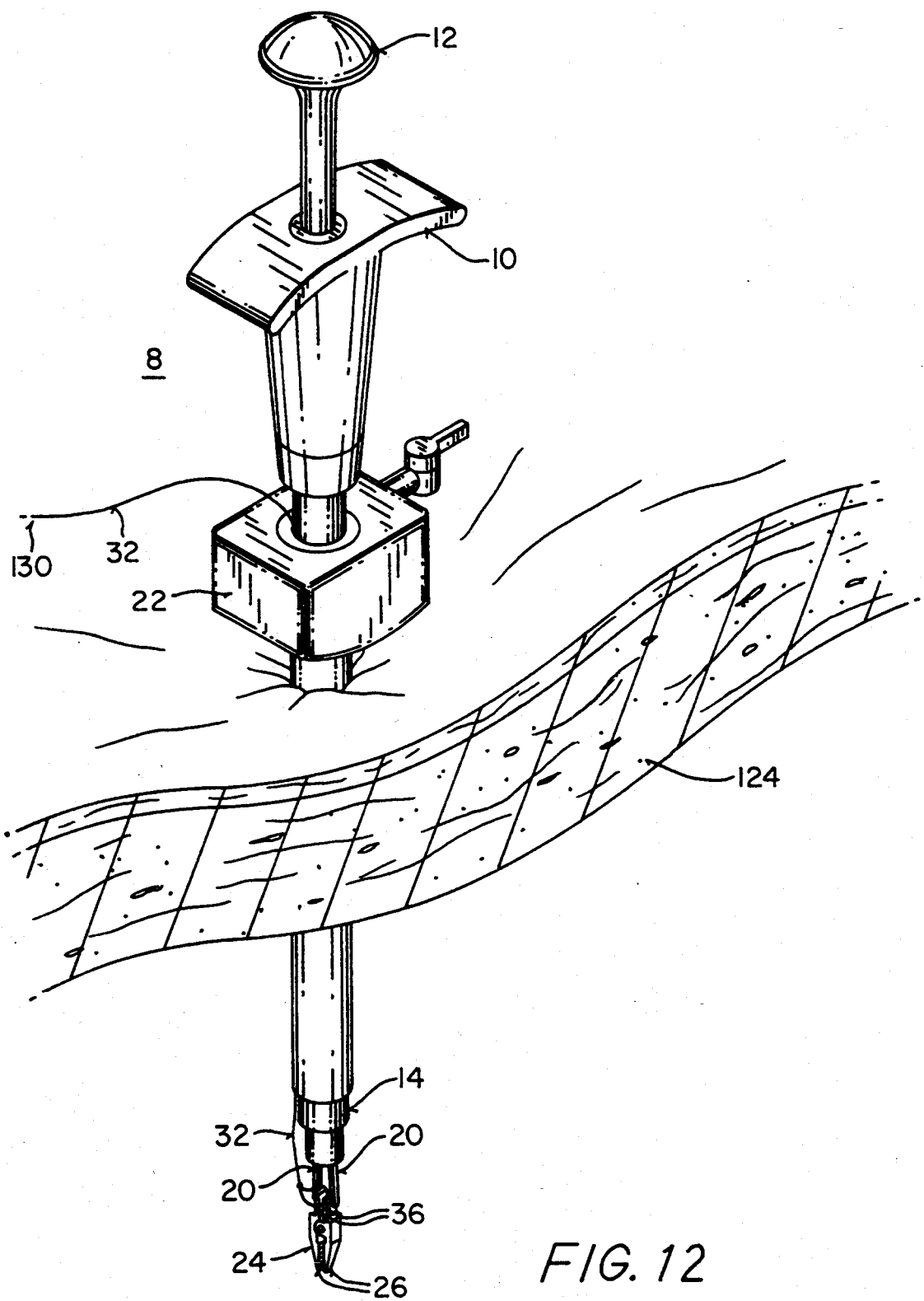
FIGS. 12-15 are perspective views of the clamp applicator of FIG. 1 positioned through a trocar sleeve in the abdominal wall in accordance with the principles of the present invention.

Referring now to FIGS. 12-23 the method of the present invention will be described. As shown in FIG. 12, a trocar sleeve 122 of well-known construction is inserted through the abdominal wall 124 using known techniques. For laparoscopic procedures, the abdominal cavity will be distended using insufflation or other technique, and a laparoscope will be positioned within the body cavity to facilitate visualization of the surgical site. Trocar sleeve 122 provides a sealed entryway into the abdominal cavity through which surgical instruments may be inserted. A clamp 24 is placed in arms 20 of the clamp applicator with tips 22 of arms 20 engaging lever arms 36 of clamp 24. Extension 14 of the clamp applicator is inserted through the trocar sleeve 122, with the free end 130 of tether 32 outside of the abdominal cavity.

Figure 13:
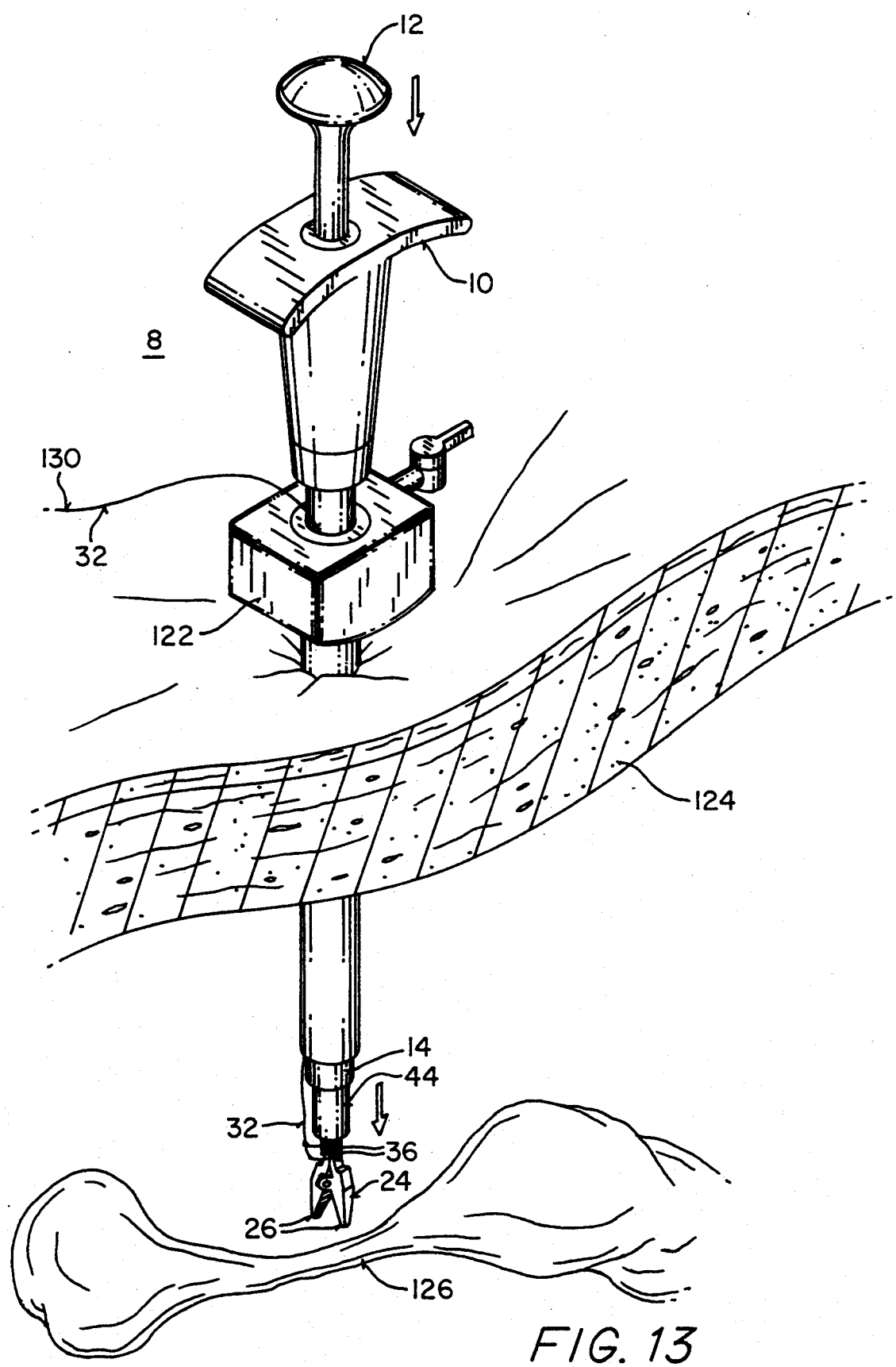

Referring now to FIG. 13, plunger 12 of the clamp applicator is depressed toward handle 10, thereby extending sleeve 44 to close arms 20 and open jaws 26 of clamp 24. The open jaws 26 are then positioned over a tissue location 126 by longitudinal, rotational and/or angular movement of clamp applicator 8.

Figure 14:
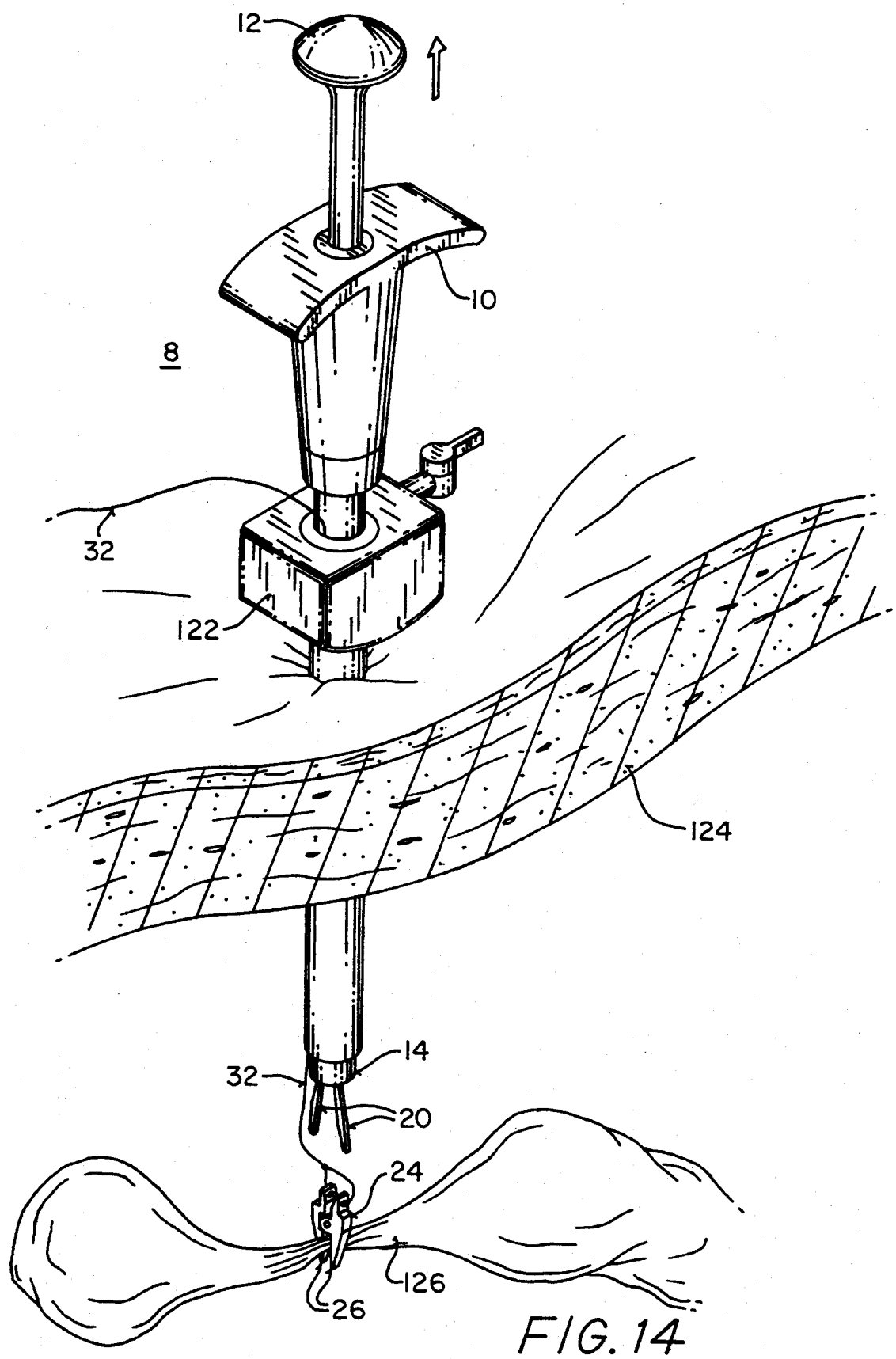

As shown in FIG. 14, when clamp 24 is positioned over tissue location 126, plunger 12 is released so as to close jaws 26 on the tissue structure and release clamp 24 from the clamp applicator.

Figure 15:
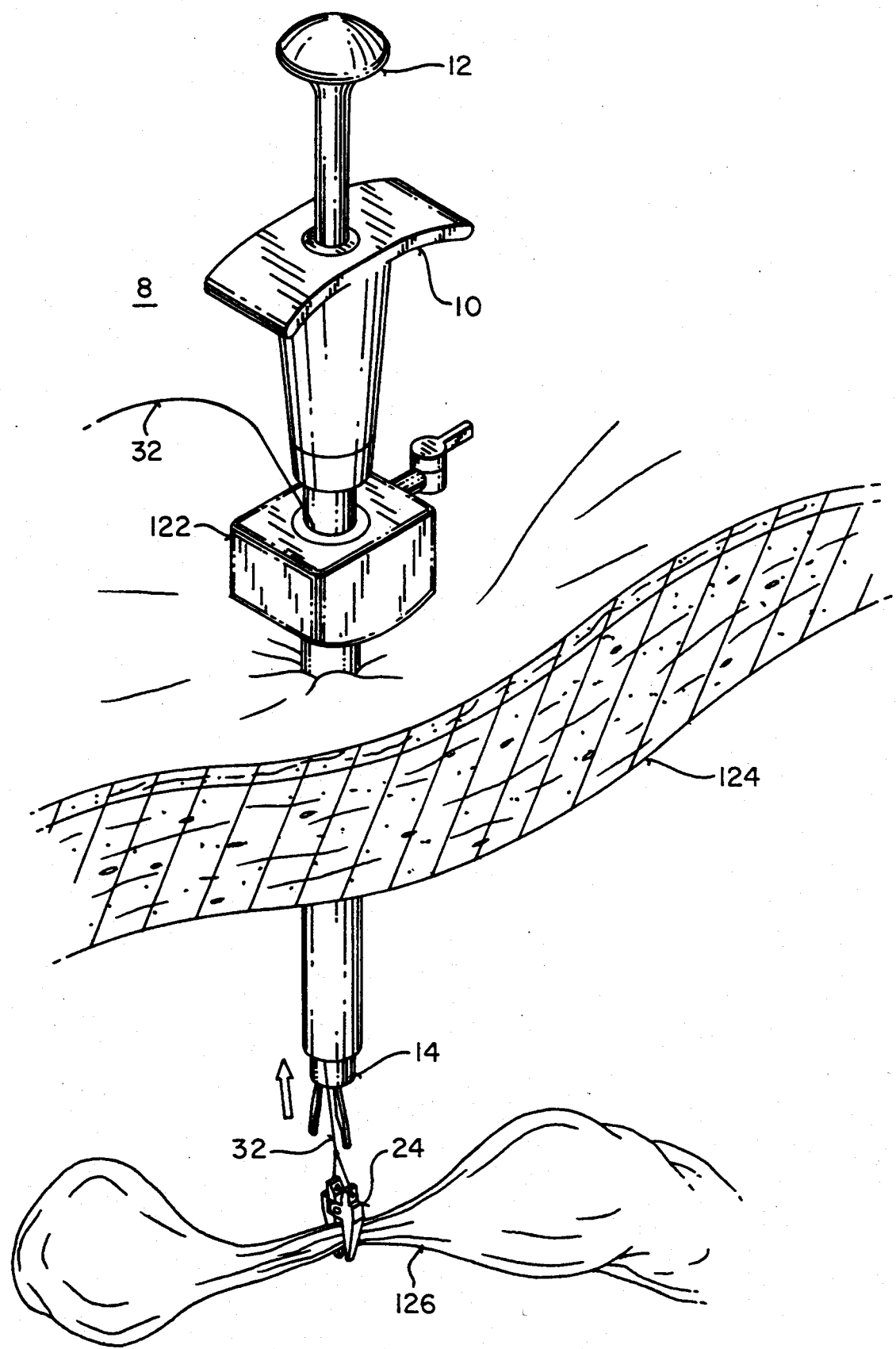

As seen in FIG. 15, clamp applicator 8 is then partially retracted from trocar sleeve 122 so as to tension tether 32 between trocar sleeve 122 and clamp 24. This facilitates retrieving tether 32 in subsequent steps.

Figure 16:
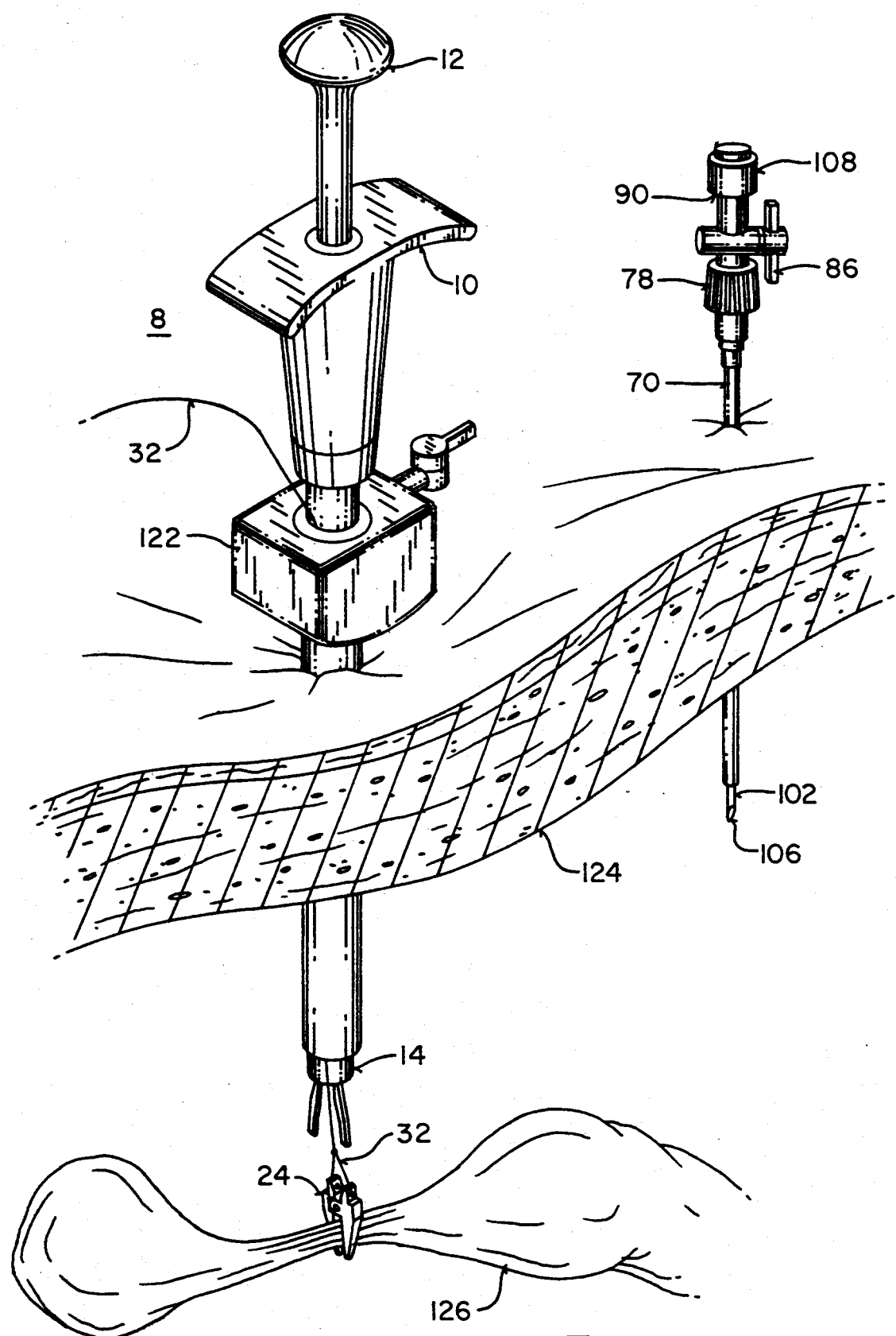
FIGS. 16-19 are perspective views of the clamp applicator of FIG. 1 positioned through a trocar sleeve in the abdominal wall with the introducer and stopcock of FIG. 7 positioned through the abdominal wall in accordance with the principles of the present invention.

As illustrated in FIG. 16, introducer/stopcock assembly 70,78 is inserted through abdominal wall 124 using obturator 102 mounted in introducer 70. Obturator 102 is secured in introducer 70 by coupling male luer lock 108 to female luer lock 90 of stopcock 78. Point 106 facilitates piercing of abdominal wall 124 for insertion of introducer 70. Alternatively, an RF electrode mounted at the distal end of introducer 70 may be used to facilitate introduction (see FIG. 7A). When the introducer/stopcock assembly is in position, obturator 102 is withdrawn and gas leakage from the abdominal cavity is prevented by closing stopcock 78 using valve handle 86.

Figure 17:
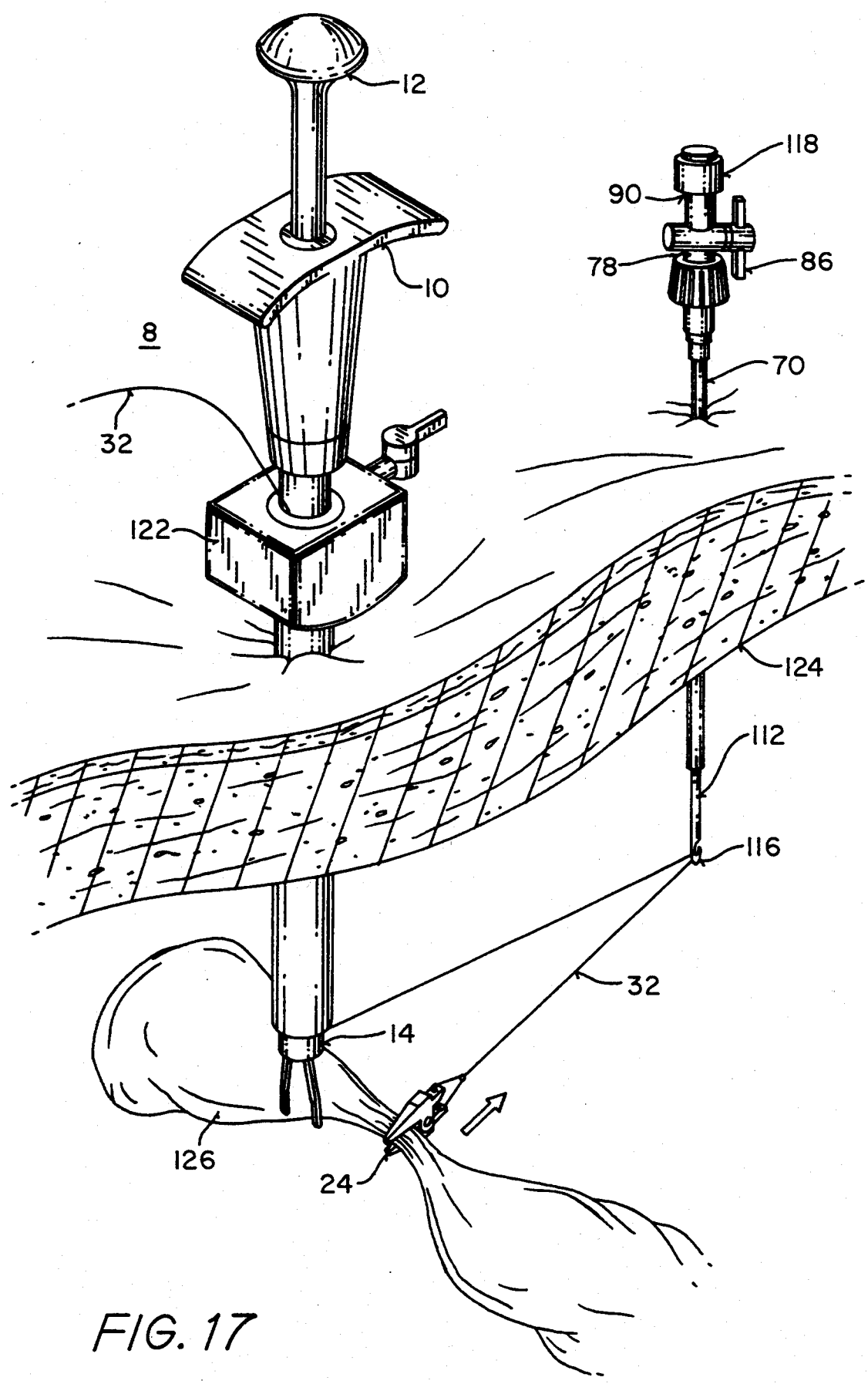

To retrieve tether 32 of clamp 24, valve handle 86 is reopened and tether snare 112 is inserted through the introducer/stopcock assembly, as shown in FIG. 17. Through angular and longitudinal manipulation of tether snare 112, hook 116 can be positioned to grasp tether 32 extending from clamp 24.

Figure 18:
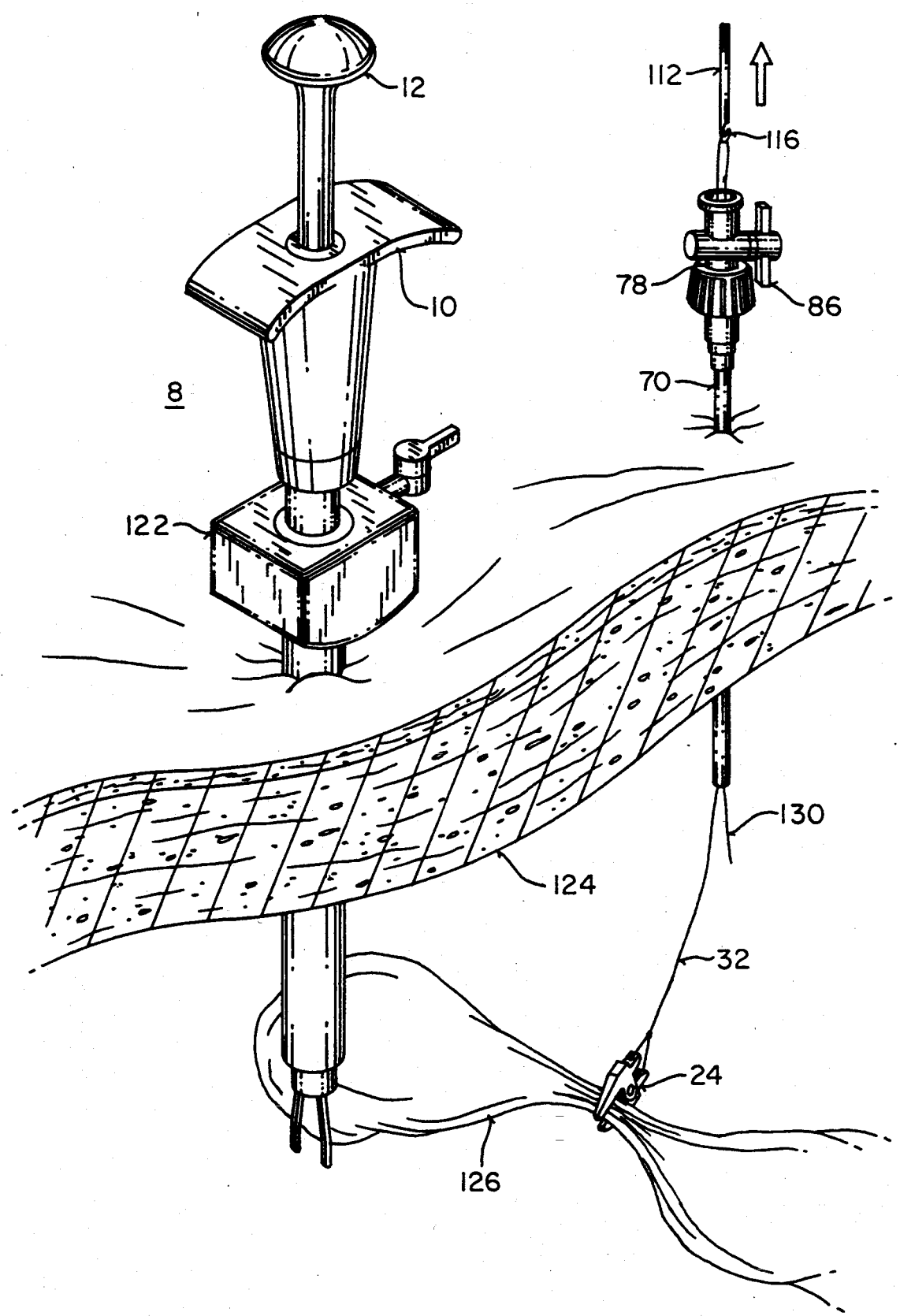

Referring now to FIG. 18, tether 32 is drawn through introducer 70 and stopcock 78 by withdrawing tether snare 112 from the introducer/stopcock assembly. Tether 32 is drawn through the introducer/stopcock assembly until free end 130 has been pulled through the proximal end of stopcock 78. The portion of tether 32 now outside of the abdominal cavity can be tensioned so as to position tissue location 126 as desired.

Figure 19:
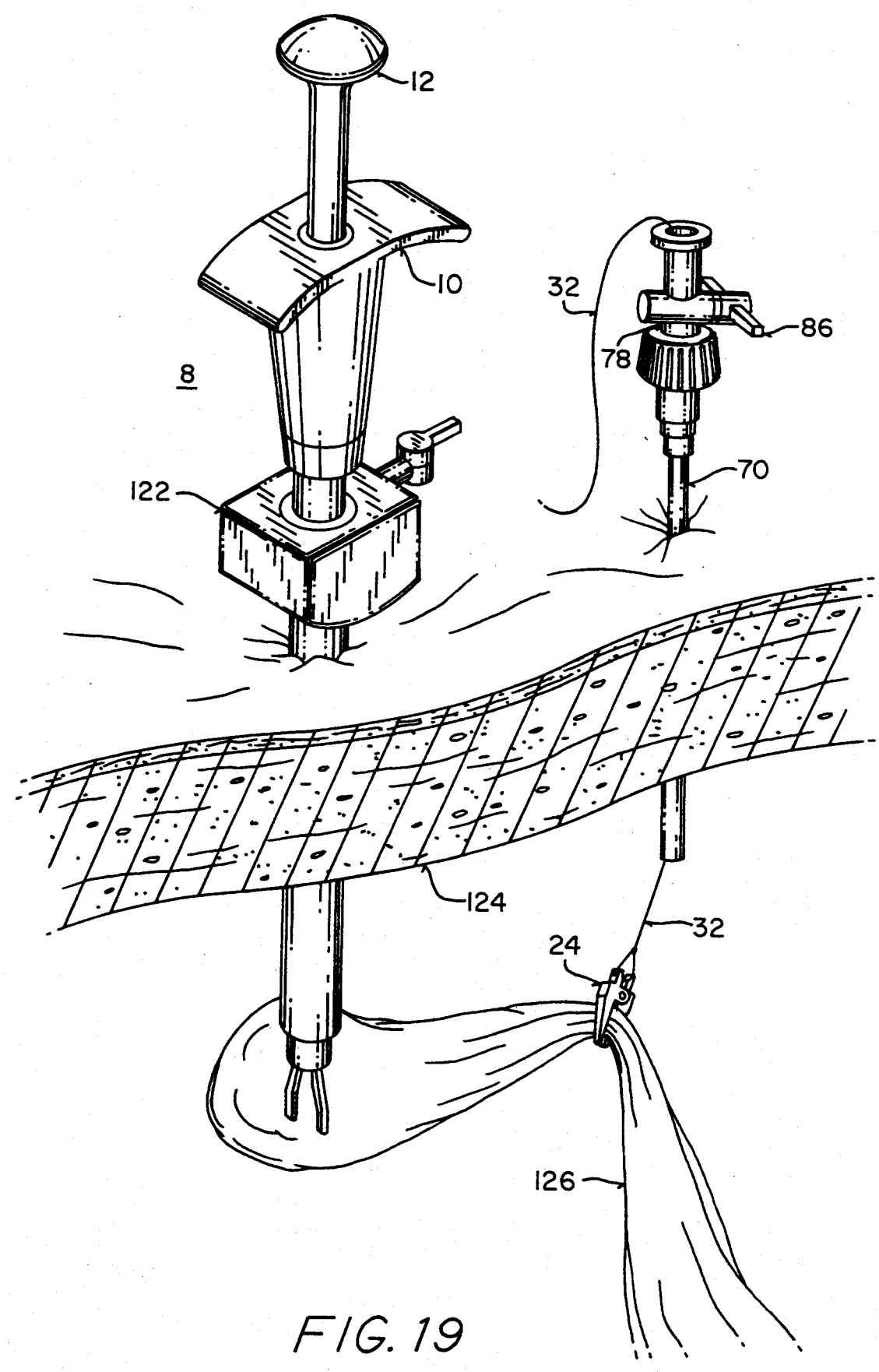

As shown in FIG. 19, when a desired position has been achieved, tether 32 can be locked in place by rotating valve handle 86 of stopcock 78, which further provides a gas-tight seal to maintain insufflation. The subsequent steps of the surgical procedure may then be performed with tissue location 126 maintained in a stationary position.

Figure 20:
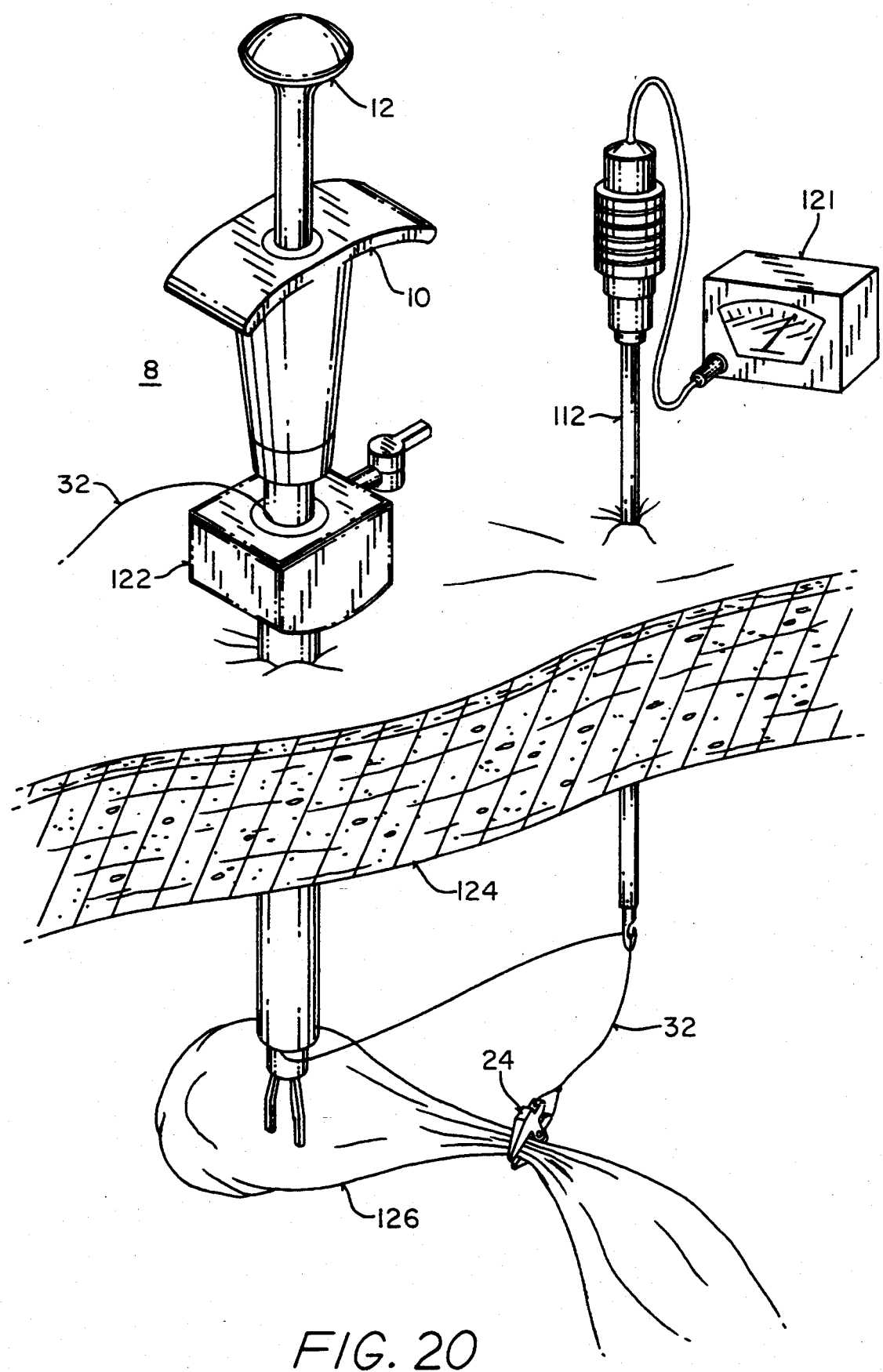
FIG. 20 is a perspective view of the clamp applicator of FIG. 1 positioned through a trocar sleeve with the tether snare of FIG. 10A introduced directly through the abdominal wall in accordance with the principles of the present invention.
Figure 21:
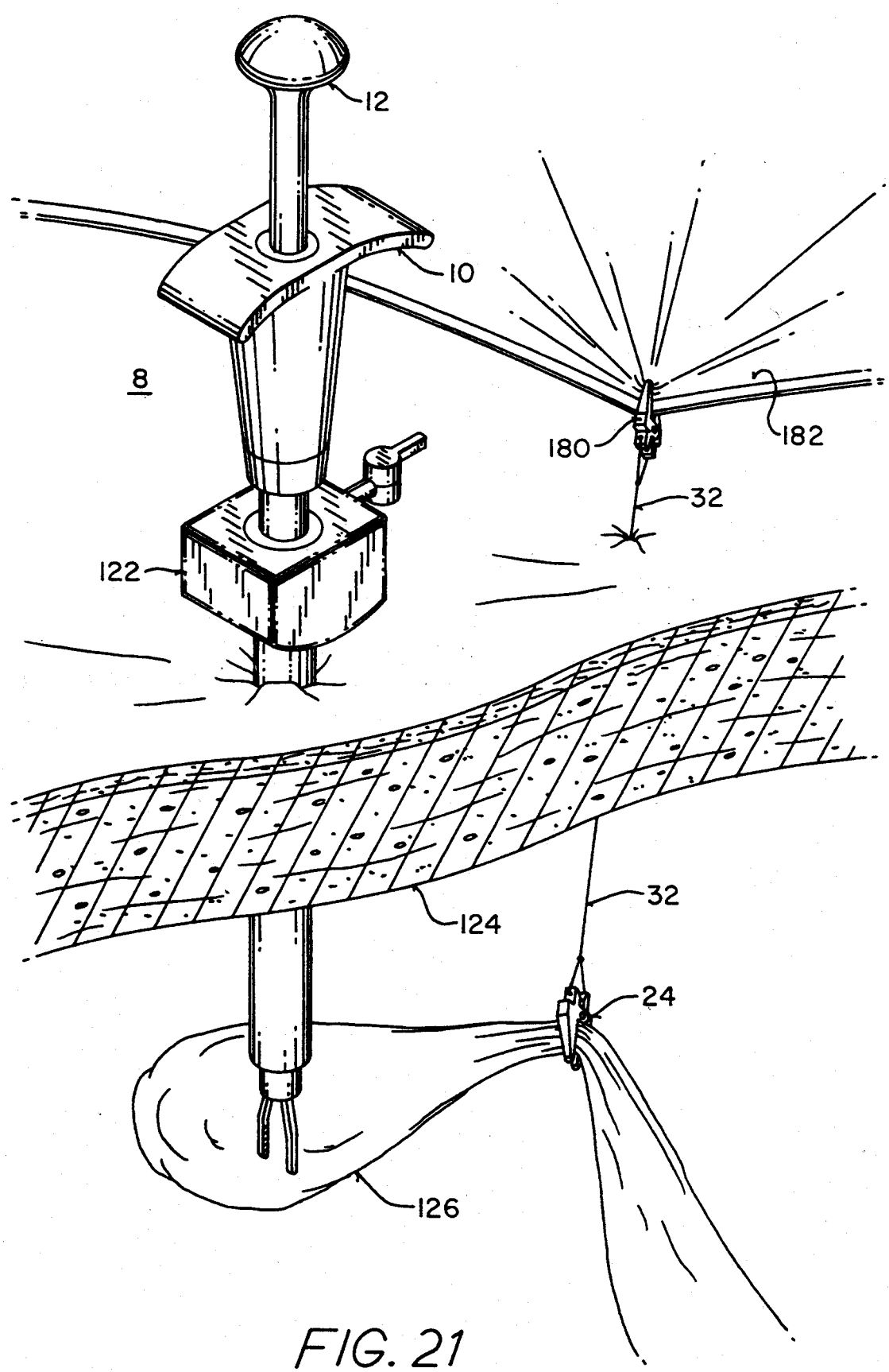
FIG. 21 is a perspective view of the clamp applicator of FIG. 1 positioned through a trocar sleeve with the tethered clamp retracting tissue by attaching the free end to an external structure.

Alternatively, tether snare 112 may be percutaneously introduced without the use of introducer 70 by direct penetration of tissue using the distal end of the snare. As illustrated in FIG. 20, tether snare 112 may have an electrode at its distal end for applying thermal, ultrasonic or RF energy to the tissue (FIGS. 9A and 20), or a sharpened distal point (FIG. 9B) for tissue penetration by exertion of a distally-directed force to the tether snare. Once introduced, the tether snare may be used to retrieve the tether and withdraw it from the body cavity, as shown in FIG. 21. A second clamp 180 may then be attached to the free end, and clamp 180 secured to an external structure such as surgical drapes 182. The free end of the tether 32 may also be secured directly to the patient's skin using a separate clamp, such as a hemostosis clamp, or other temporary fastener, such as tape.

Figure 22:
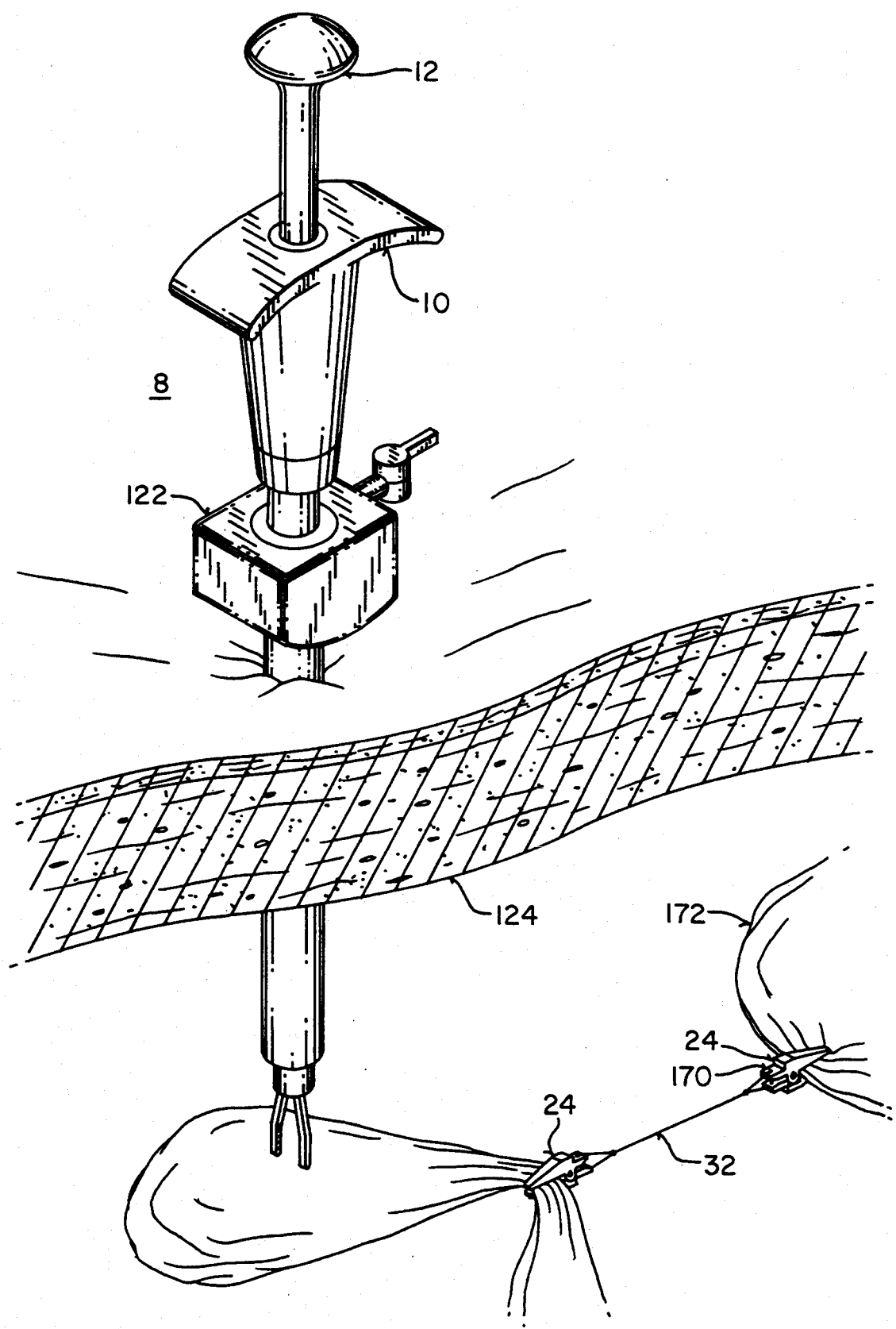
FIG. 22 is a perspective view of the clamp applicator of FIG. 1 positioned through a trocar sleeve with the tethered clamp retracting tissue by attaching the free end to an internal tissue structure.

Alternatively, as illustrated in FIG. 22, tether 32 may be left within the body cavity and coupled to a second clamp 170 or other tissue engaging means. Clamp 170 may be fastened to a second tissue location 172 to maintain the tethered clamp in a desired position.

Figure 23:
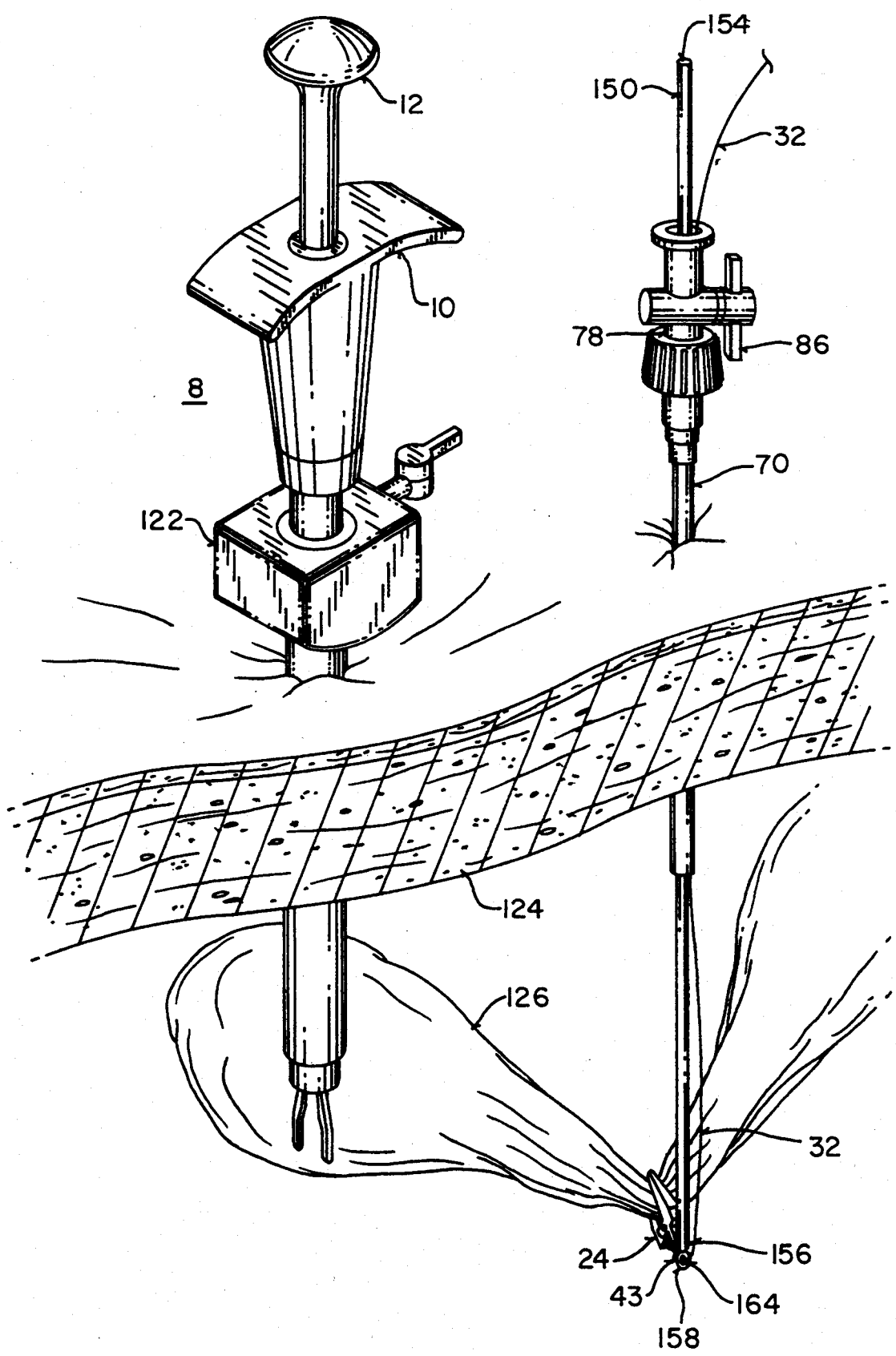
FIG. 23 is a perspective view of a body cavity illustrating the use of the positioning shaft of FIG. 11.

To position tissue 126 away from introducer 70 (and the surgeon), positioning shaft 150 is utilized, as illustrated in FIG. 23. When the free end of tether 32 has been withdrawn through introducer 70, the free end is threaded through eye 160 at the distal end of shaft 150. The positioning shaft is then introduced into the body cavity through the axial passage of the introducer. The periphery of rod 152 seals within the axial passage to prevent leakage of insufflation gas. Slight tension is maintained on the free end of the tether such that the shaft is guided along tether 32 through the introducer and toward clamp 24. The shaft is translated distally until eye 160 reaches knot 43. Knot 43 engages eye 160, such that further distal movement of shaft 150 will exert a force on clamp 24, pulling it away from the introducer to the desired position of retraction.

This facility for retraction away from the introducer makes the present invention particularly useful for retraction of the gallbladder during, for example, laparoscopic cholecystectomies. In such procedures, positioning of the introducer high in the rib cage near the diaphragm presents an undesirably high risk of injury to the patient. However, it is frequently desirable to retract the gallbladder toward the upper region of the abdomen (in the direction of the diaphragm) in such procedures. The present invention eliminates the risk associated with introduction near the diaphragm by allowing the introducer to be positioned below the ribs and, through the use of positioning shaft 160, the gallbladder may be retracted away from the introducer toward the upper portion of the abdominal cavity.

When tissue positioning is no longer required, shaft 150 is removed from the introducer, and tension on tether 32 is relieved by rotating valve handle 86 (or releasing the tissue engaging means at the free end of the tether). Clamp applicator 8 is then positioned with arms 20 over lever arms 36 of clamp 24, and plunger 12 is depressed to close arms 20 on lever arms 36, thereby opening jaws 26 of the clamp. Clamp applicator 8 is then withdrawn from trocar sleeve 122, pulling with it clamp 24 and tether 32. Valve handle 86 may then be rotated to close stopcock 78, preventing gas leakage through introducer 70.

While the above is a complete description of the preferred embodiments of the invention, various alternatives, modifications and equivalents may be used. Therefore, the above description should not be taken as limiting the scope of the invention which is defined by the appended claims.

What is claimed is:

1. A method of manipulating tissue comprising the steps of:
   introducing a clamp having one end of a flexible tether attached thereto through a percutaneous cannula to a tissue location in a body cavity so that the other end of the tether remains in the cannula;
   securing the clamp to the tissue at the tissue location;
   percutaneously introducing a rigid positioning shaft at a location on the patient distanced from the cannula;
   engaging the flexible tether with a distal end of the rigid positioning shaft;
   retracting the rigid positioning shaft until the free end of the tether is removed from the cannula to manipulate the tissue in a first direction;
   further retracting the positioning shaft until the positioning shaft and the free end of the tether are removed from the patient's body cavity; and
   introducing a positioning member along the tether and pushing on the positioning member to further manipulate the tissue in a second direction.

2. The method of claim 1 further comprising the step of securing the tether after the retracting step.

3. The method of claim 2 wherein the rigid positioning shaft is percutaneously introduced through a percutaneous introducer and wherein the step of retracting comprises pulling the free end of the tether through the percutaneous introducer.

4. The method of claim 3 wherein the step of securing the tether comprises actuating a retainer disposed at a proximal end of the introducer.

5. The method of claim 3 wherein the percutaneous introducer is positioned using an obturator removably mounted in the introducer.

6. The method of claim 3 wherein the tether is pulled through the percutaneous introducer by inserting a hook at the distal end of the positioning shaft through the introducer, engaging the tether with the hook, and retracting the positioning shaft with the tether in the hook through the introducer.

7. The method of claim 6 wherein the introducer is positioned by applying energy to tissue through an electrode at the distal end of the introducer.

8. The method of claim 7 wherein the energy is radiofrequency energy.

9. The method of claim 7 wherein the energy is ultrasonic energy.

10. The method of claim 7 wherein the energy is thermal energy.

11. The method of claim 3 wherein the distal end of the positioning shaft is introduced through an axial passage of the introducer.

12. The method of claim 11 wherein the tissue is pulled in a first direction by pulling the tether and positioned in a second direction by pushing on the positioning shaft.

13. The method of claim 11 wherein the step of introducing the clamp further comprises introducing the clamp to a tissue location having gallbladder tissue, and wherein said clamp is secured to said gallbladder tissue.

14. The method of claim 13 wherein the introducer is positioned in an abdominal region below the ribs.

15. The method of claim 11 further comprising gaseously sealing the axial passage of the introducer while the positioning shaft is positioned therethrough.

16. The method of claim 1 further comprising securing the free end of the tether to a second tissue location in the body cavity.

17. The method of claim 16 wherein the step of engaging further comprises using a hook at the distal end of the positioning shaft to engage the tether.

18. The method of claim 1 wherein the rigid positioning shaft is introduced by penetrating tissue with the distal end of the rigid positioning shaft.

19. The method of claim 18 wherein the rigid positioning shaft has a sharpened distal point to penetrate tissue.

20. The method of claim 18 wherein the rigid positioning shaft has an RF electrode on its distal end to penetrate tissue.

21. The method of claim 18 wherein the rigid positioning shaft has an ultrasonic transducer on its distal end to penetrate tissue.

22. The method of claim 18 wherein the rigid positioning shaft has a thermal electrode on its distal end to penetrate tissue.

23. The method of claim 1 further comprising passing a free end of the tether through an eye at a distal end of a positioning member and sliding the positioning member along the tether toward the clamp.

24. The method of claim 1 further comprising distending the body cavity by insufflation.

25. The method of claim 24 further comprising visualizing the tissue location using a laparoscope.

26. The method of claim 24 further comprising gaseously sealing the percutaneous cannula during the step of introducing the clamp.

27. An apparatus in kit form for tissue manipulation comprising:
   a clamp having a pair of movable jaws and means for closing and opening the jaws;
   an applicator for applying the clamp through a percutaneous cannula to a first tissue site comprising an elongated body with a distal end, a proximal end and an axial passageway therebetween, a pair of movable arms disposed at the distal end configured to engage the means for closing and opening the jaws of the clamp, means at the proximal end of the body for actuating the arms, a linkage disposed in the axial passageway, the linkage connecting the arms to the means for actuating, and means for biasing the arms in an open configuration;
   a flexible tether having a first end attached to the clamp and a free end opposite the first end for manipulating the clamp in a first direction; and
   a rigid positioning shaft having a distal end for engaging the clamp, and a proximal end for pushing on the shaft to manipulate the clamp in a second direction.

28. The apparatus as in claim 27 further comprising means for retrieving the free end of the tether.

29. The apparatus as in claim 28 wherein the means for retrieving the tether comprises an elongated snare having a hooked end for grasping the tether.

30. The apparatus as in claim 27 further comprising means separated from the clamp for securing the tether in tension so as to maintain the tissue in a desired position.

31. The apparatus as in claim 30 wherein the means for securing the tether comprises an introducer having a distal end, a proximal end and an axial passage therebetween, and a retainer disposed at the proximal end of the introducer, whereby the tether may be passed through the axial passageway and detachably secured in the retainer.

32. The apparatus as in claim 31 wherein the introducer further comprises means for gaseously sealing the axial passage.

33. The apparatus as in claim 31 wherein the retainer comprises a stopcock having a housing with a bore therethrough and a valve for closing off the bore, whereby the tether may be positioned in the bore and engaged by the valve.

34. The apparatus as in claim 30 wherein the means for securing the tether comprises means attached to the tether for detachably securing the tether to a second tissue site.

35. The apparatus as in claim 37 wherein the clamp further comprises means for biasing the jaws in a closed configuration.

36. The apparatus as in claim 27, wherein the means for actuating the arms comprises a tubular handle and a plunger slidably mounted in the handle and coupled to the linkage.

37. The apparatus as in claim 27 wherein the positioning shaft further comprises means for guiding the positioning shaft along the tether toward the clamp.

38. The apparatus as in claim 37 wherein the means for guiding comprises a loop attached to the distal end of the positioning shaft, the loop having an eye through which the free end of the tether is passed.

39. The apparatus as in claim 38 wherein the loop engages a knot in the tether near the first end.

40. An apparatus in kit form for tissue manipulation comprising:
   a clamp having a pair of movable jaws and means for opening and closing the jaws;
   a flexible tether having a first end attached to the clamp and a free end opposite the first end for manipulating the clamp in a first direction;
   an introducer having a proximal end, a distal end and an axial passage therebetween, wherein the distal end may be percutaneously positioned with the free end of the tether drawn through the axial passage; and
   a rigid positioning shaft having a rigid positioning means on a distal end for guiding the positioning shaft along the tether toward the clamp, the distal end being insertable through the axial passage while the free end of the tether is drawn through the axial passage for engaging the clamp and a proximal end for pushing on the positioning shaft to manipulate the clamp in a second direction.

41. The apparatus as in claim 40 further comprising means for holding a portion of the tether in tension.

42. The apparatus as in claim 40 wherein the means for holding comprises a stopcock disposed at the proximal end of the introducer.

43. The apparatus as in claim 40 further comprising means for retrieving the free end of the tether and drawing the free end through the axial passage of the introducer.

44. The apparatus as in claim 43 wherein the means for retrieving and drawing comprises an elongated snare having a hooked end configured to pass through the axial passage of the introducer.

45. The apparatus as in claim 40 further comprising means for percutaneously inserting the introducer.

46. The apparatus as in claim 45 wherein the means for inserting the introducer comprises an obturator removably disposed in the axial passage of the introducer.

47. The apparatus as in claim 40 further comprising means for applying the clamp to the tissue through a percutaneous cannula.

48. The apparatus as in claim 47 wherein the means for applying comprises:
   an elongated body having a distal end, a proximal end and an axial passageway therebetween;
   a pair of movable arms disposed at the distal end of the body configured to engage the means for opening and closing the jaws of the clamp;
   means at the proximal end of the body for actuating the arms; and
   a linkage disposed in an axial passageway and connecting the arms to the means for actuating.

49. The apparatus as in claim 48, wherein the means for actuating the arms comprises a tubular handle and a plunger slidably mounted in the handle and coupled to the linkage.

50. The apparatus as in claim 40 wherein the introducer includes means for gaseously sealing the axial passage.

51. The apparatus as in claim 40 wherein the means for guiding comprises a loop attached to the distal end of the positioning shaft, the loop having an eye through which the free end of the tether is passed.

52. The apparatus as in claim 51 wherein the first end of the tether is connected to the clamp by a knot.

53. The apparatus as in claim 52 wherein the loop at the distal end of the positioning shaft is rigid to assist in engaging the knot.

54. The apparatus as in claim 40 wherein the means for opening and closing the jaws of the clamp comprises a pair of levers attached to the jaws and connected by a hinge disposed between the levers and the jaws.

55. An apparatus in kit form for tissue manipulation comprising:
   a clamp having a pair of movable jaws and means for opening and closing the jaws;
   a flexible tether having a first end directly attached to the clamp and a free end opposite the first end for manipulating the clamp in a first direction;
   means for percutaneously applying the clamp to the tissue;
   an introducer separate from the clamp applying means having a proximal end, a distal end and an axial passage therebetween, whereby the tether may be passed through the axial passage;
   a rigid positioning shaft having a rigid distal end insertable through the axial passage while the tether extends through the passage for engaging the clamp and a proximal end for pushing on the positioning shaft to manipulate the clamp in a second direction; and
   means on the proximal end of the introducer for retaining the tether which passes through the axial passage.

56. The apparatus as in claim 55 wherein the means for applying comprises:
   an elongated body having a distal end, a proximal end and an axial passageway therebetween;
   a pair of movable arms disposed at the distal end of the body configured to engage the means for opening and closing the jaws of the clamp;
   means at the proximal end of the body for actuating the arms; and
   a linkage disposed in the axial passageway and connecting the arms to the means for actuating.

57. The apparatus as in claim 56, wherein the means for actuating the arms comprises a tubular handle and a plunger slidably mounted in the handle and coupled to the linkage.

58. The apparatus as in claim 56 wherein the means for applying a clamp further comprises means for biasing the arms in an open configuration.

59. The apparatus as in claim 55 further comprising means for retrieving the free end of the tether and drawing the free end through the axial passage of the introducer.

60. The apparatus as in claim 59 wherein the means for retrieving the free end comprises an elongated snare with a hooked end configured to pass through the axial passage of the introducer.

61. The apparatus as in claim 60 wherein the snare comprises means at a distal end thereof for penetrating tissue to facilitate percutaneous introduction of the snare.

62. The apparatus as in claim 61 wherein the means for penetrating comprises a sharpened point.

63. The apparatus as in claim 61 wherein the means for penetrating comprises means for applying energy to tissue.

64. The apparatus as in claim 63 wherein the means for applying energy comprises an RF electrode.

65. The apparatus as in claim 63 wherein the means for applying energy comprises an ultrasonic transducer.

66. The apparatus as in claim 63 wherein the means for applying energy comprises a thermal electrode.

67. The apparatus as in claim 55 further comprising means for percutaneously inserting the introducer into a patient.

68. The apparatus as in claim 67 wherein the means for inserting the introducer comprises an obturator having a distal point for piercing tissue.

69. The apparatus as in claim 67 wherein the means for inserting the introducer comprises means disposed at the distal end of the introducer for applying energy to tissue so as to penetrate therethrough.

70. The apparatus as in claim 69 wherein the means for applying energy comprises a radiofrequency electrode.

71. The apparatus as in claim 69 wherein the means for applying energy comprises an ultrasonic transducer.

72. The apparatus as in claim 69 wherein the means for applying energy comprises a thermal electrode.

73. The apparatus as in claim 55 wherein the clamp further comprises means for biasing the jaws in a closed configuration.

74. The apparatus as in claim 55 wherein the introducer includes means for gaseously sealing the axial passage.

75. The apparatus as in claim 55 wherein the positioning shaft further comprises means for guiding the positioning shaft along the tether toward the clamp.

76. The apparatus as in claim 75 wherein the means for guiding comprises a loop attached to the distal end of the positioning shaft, the loop having an eye through which the free end of the tether is passed.

77. The apparatus as in claim 76 wherein the first end of the tether is connected to the clamp by a knot.

78. The apparatus as in claim 77 wherein the loop at the distal end of the positioning shaft is rigid to assist in engaging the knot.

79. The apparatus as in claim 55 wherein the means for opening and closing the jaws of the clamp comprises a pair of levers attached to the jaws and connected by a hinge disposed between the levers and the jaws.

* * * * *